US012661137B2

(12) United States Patent
Razdan

(10) Patent No.: US 12,661,137 B2
(45) Date of Patent: Jun. 23, 2026

(54) UMBRELLA CATHETER DEVICE

(71) Applicant: Rishi Razdan, Jacksonville, FL (US)

(72) Inventor: Rishi Razdan, Jacksonville, FL (US)

( * ) Notice: Subject to any disclaimer, the term of this patent is extended or adjusted under 35 U.S.C. 154(b) by 944 days.

(21) Appl. No.: 17/812,495

(22) Filed: Jul. 14, 2022

(65) Prior Publication Data

US 2024/0016509 A1 Jan. 18, 2024

(51) Int. Cl.
*A61B 17/221* (2006.01)
*A61B 17/00* (2006.01)

(52) U.S. Cl.
CPC .. *A61B 17/221* (2013.01); *A61B 2017/00292* (2013.01); *A61B 2017/00367* (2013.01); *A61B 2017/2212* (2013.01)

(58) Field of Classification Search
CPC .................... A61B 17/221; A61B 2017/00292
See application file for complete search history.

(56) References Cited

U.S. PATENT DOCUMENTS

| | | | |
|---|---|---|---|
| 3,445,879 A | 5/1969 | Taylor | |
| 3,472,230 A | 10/1969 | Fogarty | |
| 4,741,335 A * | 5/1988 | Okada | A61B 17/221 |
| | | | 606/127 |
| 5,788,710 A * | 8/1998 | Bates | A61B 17/221 |
| | | | 606/127 |

| | | | |
|---|---|---|---|
| 5,910,144 A * | 6/1999 | Hayashi | A61F 2/95 |
| | | | 606/191 |
| 6,136,016 A | 10/2000 | Barbut et al. | |
| 6,168,603 B1 | 1/2001 | Leslie et al. | |

(Continued)

FOREIGN PATENT DOCUMENTS

| | | |
|---|---|---|
| ES | 2239902 A1 | 10/2005 |
| WO | 2010024801 A1 | 3/2010 |

(Continued)

OTHER PUBLICATIONS

International Search Report and Written Opinion of the International Searching Authority; Application No. PCT/US23/070237; Completed: Nov. 8, 2023; Mailing Date: Mar. 1, 2024; 14 Pages.

(Continued)

*Primary Examiner* — Erin McGrath
(74) *Attorney, Agent, or Firm* — Jacob M. Ward; Ward Law Office LLC

(57) ABSTRACT

A catheter device includes an inner tube, an outer tube disposed around the inner tube, a capturing tool connected to a distal end of the inner tube and having a mesh adapted to capture an object within a body passage, a handle connected to a proximal section of the inner tube and configured to retract the outer tube in a proximal direction relative to the inner tube to expose the capturing tool, and a driver connecting the capturing tool to the handle and configured to transmit a force from the handle to the capturing tool to actuate the capturing tool from an expanded position towards a collapsed position, the driver being disposed between the inner and outer tubes. The capturing tool is biased towards the expanded position such that the capturing tool automatically transitions into the expanded position in response the outer tube being retracted in the proximal direction.

14 Claims, 22 Drawing Sheets

(56) References Cited

U.S. PATENT DOCUMENTS

| | | | | |
|---|---|---|---|---|
| 6,348,056 | B1 * | 2/2002 | Bates ................... | A61B 17/221 |
| | | | | 606/113 |
| 7,780,696 | B2 | 8/2010 | Daniel et al. | |
| 8,382,908 | B2 | 2/2013 | Vazales et al. | |
| 2002/0002383 | A1 * | 1/2002 | Sepetka ................... | A61F 2/013 |
| | | | | 606/191 |
| 2003/0093072 | A1 | 5/2003 | Friedman | |
| 2004/0148021 | A1 | 7/2004 | Cartledge et al. | |
| 2006/0195118 | A1 * | 8/2006 | Richardson .......... | A61B 17/221 |
| | | | | 606/113 |
| 2010/0087908 | A1 | 4/2010 | Hilaire et al. | |
| 2010/0152519 | A1 | 6/2010 | White et al. | |
| 2010/0211094 | A1 | 8/2010 | Sargent, Jr. | |
| 2011/0313451 | A1 | 12/2011 | Hruska et al. | |
| 2014/0257245 | A1 | 9/2014 | Rosenbluth et al. | |
| 2014/0277086 | A1 | 9/2014 | Hagan | |
| 2014/0364941 | A1 | 12/2014 | Edmiston et al. | |
| 2016/0235422 | A1 * | 8/2016 | Al-Jilaihawi .......... | A61B 17/50 |
| 2017/0112513 | A1 | 4/2017 | Marchand et al. | |
| 2017/0112514 | A1 * | 4/2017 | Marchand ............ | A61B 17/221 |
| 2021/0023248 | A1 | 1/2021 | Townsend et al. | |
| 2021/0154433 | A1 | 5/2021 | Casey et al. | |
| 2021/0213248 | A1 | 7/2021 | Razdan, M.D. | |

FOREIGN PATENT DOCUMENTS

| | | | |
|---|---|---|---|
| WO | 2017074530 | A1 | 5/2017 |
| WO | 2021141683 | A1 | 7/2021 |

OTHER PUBLICATIONS

Cook Medical, Urology, Aug. 26, 2014, Our History: Nitinol stone extractors, NTrap Stone Entrapment and Extraction Device; https://www.cookmedical.com/urology/our-history-nitinol-stone-extractors/; Accessed: Jan. 10, 2020; 3 Pages.

Actment Co., Ltd.; http://www.actment.co.jp/publics/index/103/; Accessed: Jan. 10, 2020; 6 Pages.

International Preliminary Report on Patentabiltiy; Application No. PCT/US2020/061207; Completed: Nov. 8, 2021; 21 Pages.

Nordson Medical—Nitinol Components; https://www.nordsonmedical.com/Components-and-Technologies/Nitinol-Components/; Accessed: Jan. 10, 2020; 4 Pages.

International Search Report and Written Opinion of the International Searching Authority; Application No. PCT/US20/61207; Completed Jan. 19, 2021; Issued: Feb. 12, 2021; 8 Pages.

* cited by examiner

108

UMBRELLA CATHETER DEVICE

TECHNICAL FIELD

The disclosure herein relates to devices used to clear obstructions and objects in veins, arteries and any other tubular structure within the body. Obstructions can form in arteries and veins when a catheter is inserted for permanent or semi-permanent treatments. Fibrin sheaths or thrombus can form around the outer surface of a hemodialysis catheter, reducing or even completely blocking flow through either lumen or the catheter. The present disclosure more specifically relates to a catheter for removing fibrin sheaths, embolisms, or any other objects inside of an artery, vein, or other structure with a lumen. The present disclosure relates to devices that expand within a vein, artery, or lumen or a bodily structure to capture objects or material for removal while still allowing flow through the passage.

BACKGROUND

Devices known in the art allow a surgeon to remove objects from a passage within a body. These devices can include netting made of wires, the netting expanding and contracting to form different shapes. The netting can be made of materials that expand, contract, and bend in ways that allow the net to form different shapes within a passage. Such device requires more than one hand to open and close to capture objects, limiting the tasks a user can perform while actuating the device.

It is important for such device in the field to be uniquely suited for the passages or bodily structures in which it is intended to be used in because of the delicate nature of the tissues and/or organs that the device may contact. The device must also be simple and easy to use with one hand. There is a wide variety of procedures that are carried out in veins and arteries, each with their own requirements for stiffness of the wire net, controllability of the expansion and contraction of the wire net, visibility of the wire net on imaging machines, the device's ability to remove or install an object, and the device's ability to effectively handle and manipulate the size, shape, and consistency of the object in the passage. Applicant addresses these problems and more by providing a device that can be actuated with one hand while a user's other hand is free to guide the device through a passage or perform other functions simultaneously with actuation.

SUMMARY

The needs set forth herein as well as further and other needs and advantages are addressed by the present embodiments, which illustrate solutions and advantages described below.

It is an object of the present teachings to provide a device that can be inserted into a vein, artery, or other passage in a body and be expanded in an umbrella shape to capture an object in the body passage and allow a surgeon to withdraw the object with the device.

It is an object of the present teachings to provide a medical device that is insertable into an intravascular system and configured for actuation by a single hand of the user to capture and remove an object located within the intravascular system.

It is an object of the present teachings to provide a catheter device that is small enough in cross sectional diameter to be inserted into a body passage and long enough to reach an object or obstruction. In addition to being able to capture the object or obstruction, the catheter device may be adapted to allow fluid flow through the body passage when the device is in an expanded state.

It is an object of the present teaching to provide a catheter device that can capture an object in a body passage and secure the object to the distal end of the device to ensure removal of the object during withdrawal of the catheter device from the body passage.

These and other objects of the present teachings are achieved by providing a catheter device comprising: an inner tube having a proximal end and a distal end; an outer tube disposed around the inner tube; a capturing tool connected to the distal end of the inner tube, the capturing tool including a mesh adapted to capture an object within a body passage, the outer tube being configured to cover at least a portion of the capturing tool; a handle connected to a proximal section of the inner tube and configured to retract the outer tube in a proximal direction relative to the inner tube to expose the capturing tool; and a driver connecting the capturing tool to the handle and configured to transmit a force from the handle to the capturing tool to actuate the capturing tool from an expanded position towards a collapsed position, the driver being disposed between the inner tube and the outer tube. The capturing tool is biased towards the expanded position such that the capturing tool automatically transitions into the expanded position in response the outer tube being retracted in the proximal direction.

The present teachings also provide a catheter device, comprising: an inner tube having a proximal end and a distal end; a capturing tool fixed to the distal end of the inner tube, the capturing tool includes a mesh adapted to capture an object within a bodily passage and a plurality of ribs that have first ends distributed around a circumference of the inner tube and second ends connected to the mesh, wherein the mesh is configured to cover a top-side of each rib; a spring guide disposed around the inner tube and proximate to the capturing tool, the spring guide having at least one link connected to the second ends of the ribs, the spring guide being configured to slide along the inner tube; a spring wrapped around a distal section of the inner tube and having a distal end that abuts the spring guide to press the spring guide towards the capturing tool; a handle connected to a proximal section of the inner tube; and at least one driver extending from the handle to the spring guide and being configured to transmit a force from the handle to the capturing tool via the at least one link of the spring guide to actuate the capturing tool from an expanded position towards a collapsed position, wherein the spring biases the capturing tool towards the expanded position.

The present teachings further provide a catheter device that has an inner tube and an outer tube, both with proximal and distal ends. The device also has a driver(s) extending alongside the inner tube from a proximal area of the inner tube to a capturing tool at the distal end of the inner tube. The capturing tool includes a plurality of ribs, a mesh, and a fitting. Each rib has a first end connected to the fitting at a first connection point and a second end opposite the first end. The mesh wraps around an outer side of each of the ribs and is connected to each of the ribs at the second end. The fitting is mounted to the inner tube, and more specifically the distal end of the inner tube. The device also has a handle disposed at the proximal ends of the inner tube and, the outer tube. The handle includes a base, a first grip member, a second grip member, and a rotatable fixture. The first grip member is disposed at a distal section of the base, while the second grip member is disposed at a proximal end of the base. The rotatable fixture is located proximate to the first grip member, at a distal end of the base. In some embodiments, the drivers can connect the first grip member to the ribs, wherein the drivers actuate the plurality of ribs and the mesh from an expanded/open position to a collapsed/closed position relative to the inner tube in response to moving the first grip member relative to the second grip member. In other embodiments, drivers connect the first grip member to a spring guide, wherein the spring guide is attached to guide wires that are connected to the ribs. The drivers may comprise, for example, one or more linkages, force transmission rods, push-pull rods, force transmission cables, sutures, or the like.

The catheter device may be configured such that the first grip member actuates the plurality of ribs by longitudinal movement of the drivers.

The catheter device may be configured such that the second grip member is configured to pivot around an axis of the proximal end of the handle base for ergonomic support.

The rotatable fixture is configured to retract the outer tube, for example in a proximal direction towards the handle, which in turn exposes the capturing tool located at the distal end of the inner tube. The outer tube thus protects the capturing tool before the capturing tool is deployed. Prior to being deployed, the capturing tool is in a collapsed/closed state inside the outer tube. In some embodiments, the ribs of the capturing tool are biased in or towards the expanded position so that they automatically expand out and away from the inner tube once the outer tube is retracted. In other embodiments, the ribs may be biased in or towards the collapsed state so that they remain substantially alongside or adjacent the inner tube (e.g., in contact with the outer surface of the inner tube) when the outer tube is retracted.

In some embodiments, the handle base houses a spring, which is in a loaded condition when the ribs are in the closed or collapsed position. The spring is in an unloaded condition when the ribs are in the expanded or open position. In other embodiments, the spring may be configured in an opposite manner, such that it is in an unloaded condition when the ribs are in an open or expanded position, and a loaded condition when the ribs are in a closed or collapsed position.

One or more ribs of the plurality of ribs may extend in an arc-shape from the fitting of the capturing tool.

The capturing tool includes at least three ribs that are positioned equidistant from each other around the circumference of the fitting and in turn around the circumference of the inner tube. For example, the capturing tool may have six ribs disposed equidistant from each other around the fitting. In some embodiments, the capturing tool may have only two ribs around which the mesh wraps and is connected to respective second ends of the ribs.

In some embodiments, each rib of the plurality of ribs may have an atraumatic tip at the second end. The atraumatic tip may be made of a polymer material.

The plurality of ribs may be constructed of one or more shape-memory alloys.

In some embodiments, the plurality of ribs may be welded to the fitting of the capturing tool at the first connection points. In other embodiments, the plurality of ribs may be inserted into the fitting of the capturing tool, and for example, into recesses formed in the exterior surface of the fitting.

The mesh may include a plurality of filaments. The filaments may be woven. For example, the filaments of the mesh may have a plain weave pattern, twill weave pattern, a stain weave pattern, a basket weave pattern, or a leno weave pattern. In other embodiments, the filaments of the mesh may be knitted.

In some embodiments, at least one filament of the mesh is connected to the second ends of at least two or more ribs. In other embodiments, at least one filament of the mesh is connected to the second ends of all the ribs.

In some embodiments, the inner tube, the outer tube, and/or the drivers may be flexible. In other embodiments, the inner tube, the outer tube, and/or the drivers may be rigid. Still further, in other embodiments, one or two of these components are flexible, while the remaining component(s) is/are rigid.

The handle is configured to control the plurality of ribs in transitioning between the expanded position and the collapsed position by transmitting a force via the drivers. In particular, by actuating the first grip member relative to the second grip member (e.g., moving the first grip towards the second grip member), a force is exerted by the user through the grip members, wherein the force is transferred to the drivers. In some embodiments, the force from the drivers is transmitted directly to the ribs; whereas in other embodiments, the force is transmitted to a spring guide which in turn transmits the force to guide wires connected to the ribs.

Additional features and aspects of the present teachings will become apparent from the following detailed description, taken in conjunction with the accompanying drawings, which illustrate by way of example the features in accordance with embodiments of the present teachings. The summary is not intended to limit the scope of the present teachings.

BRIEF DESCRIPTION OF THE DRAWINGS

FIG. 10 is a front view of the guide wire of FIG. 9a.

FIG. 11 is a magnified view of the capturing tool of FIG. 9a, wherein the guide tube has hollow passages in which the drivers extend through.

It should be understood that through the drawings, corresponding reference numerals indicate like or corresponding parts and features.

DETAILED DESCRIPTION

Figure 1A:
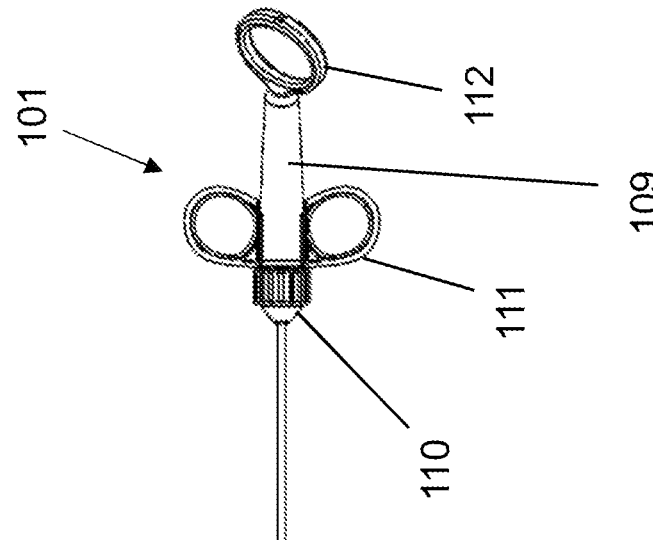
FIG. 1*a* is a top view of a catheter device according to the present teachings, and in particular the catheter device having a distal capturing tool shielded within an outer tube.
Figure 1A:
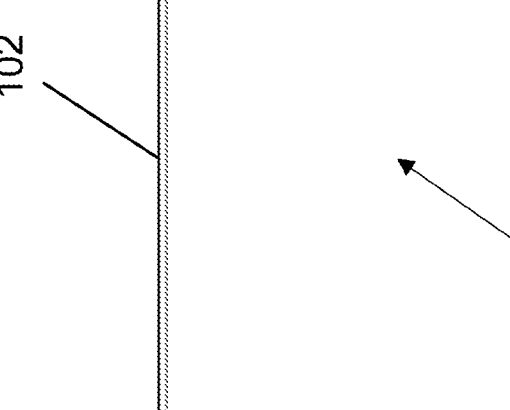

The present teachings are described more fully hereinafter with reference to the accompanying drawings, in which the present embodiments are shown. The following description is presented for illustrative purposes only and the present teachings should not be limited to these embodiments.

In compliance with the statute, the present teachings have been described in language more or less specific as to structural and mechanical features. It is to be understood, however, that the present teachings are not limited to the specific features shown and described, since the devices, systems, and methods herein disclosed comprise preferred forms of putting the present teachings into effect.

For purposes of explanation and not limitation, specific details are set forth such as particular structures, architectures, interfaces, techniques, etc. in order to provide a thorough understanding. In other instances, detailed descriptions of well-known devices and methods are omitted so as not to obscure the description with unnecessary detail.

Generally, all terms used in the claims are to be interpreted according to their ordinary meaning in the technical field, unless explicitly defined otherwise herein. All references to a/an/the element, apparatus, component, means, step, etc. are to be interpreted openly as referring to at least one instance of the element, apparatus, component, means, step, etc., unless explicitly stated otherwise. The steps of any method disclosed herein do not have to be performed in the exact order disclosed, unless explicitly stated. The use of "first", "second," etc. for different features/components of the present disclosure are only intended to distinguish the features/components from other similar features/components and not to impart any order or hierarchy to the features/components.

A notable advantage of the catheter device according to the present teachings is the ability to securely capture an object within a body passage and withdraw the object with the device while only minimally restricting fluid flow through the body passage. Another notable advantage of the catheter device includes the ability to retrieve obstructive objects while maintaining venous or arterial access via an intraluminal wire extending within a central lumen or flush port of the device. Another notable advantage of the catheter device includes the ability to detach the capturing tool and exchange it with another capturing tool. This detachable configuration allows for a clean capturing tool to be connected to the catheter device and thus allows for quick turn-around of the catheter device between medical procedures by enabling use of the same handle. The detachable configuration also enables the catheter device to be equipped with different capturing tools having umbrella-shaped nets of varying diameters to adequately oppose large-diameter vessel walls or small-diameter vessel walls, depending on the requirements of the medical procedure. Additionally, a notable advantage of the catheter device is a self-centering nature of the capturing tool within a body passage or lumen due to a radial force (e.g., minimal force) exerted by the capturing tool against the interior walls of the body passage or lumen.

Referring to FIG. 1a, a catheter device 100 is shown. The catheter 100 may be designed to remove an object or obstruction within a body passage (e.g., vein, artery, vessel, lumen, or other tubular structure of the body). In addition, or alternatively, the catheter 100 may be designed to insert and place an object within the body passage. The catheter device 100 comprises a handle 101, and outer tube 102 connected to the handle 101, an inner tube 104 (see FIG. 1b) disposed within a bore of the outer tube 102, and a capturing tool 103 (see FIG. 1b) connected to the inner tube 104. The outer tube 102 and the inner tube 104 may be concentric with each other. However, in other embodiments, the inner tube 104 may be set eccentric relative to the outer tube 102. FIG. 1a shows one of several states of the catheter device, where the entire inner tube 104 and the capturing tool 103 are situated within the outer tube 102 and thus are shielded/protected by outer tube 102. The handle 101 is designed to be grasped by a single hand of the user, and more specifically, is designed so that only hand is required to manipulate the catheter device. The handle 101 has several structural elements, including but not limited to a first grip member 111 (e.g., finger loops), a second grip member 112, and a rotatable fixture 110, that enable mechanical adjustment of the catheter device between different states/positions.

Figure 1B:
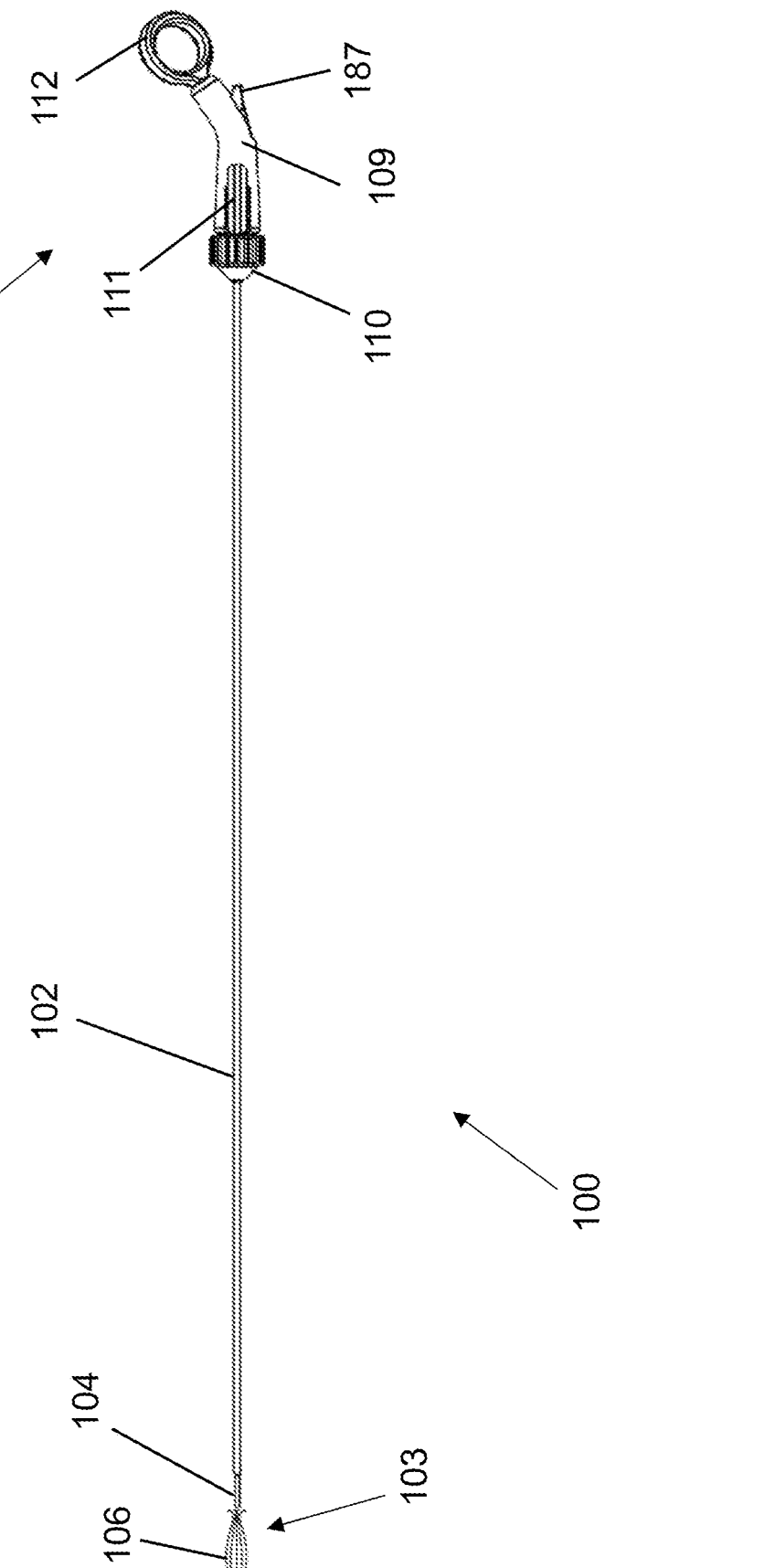
FIG. 1*b* is a cross-sectional view of the catheter device of FIG. 1, wherein the capturing tool is exposed outside the outer tube and is placed in a closed position.

Referring to FIG. 1b, the catheter device 100 is shown wherein the capturing tool is exposed outside the outer tube and is placed in a closed position (e.g., after having captured an object). At the beginning of a medical procedure, the entire inner tube 104 and the capturing tool 103 are typically situated within the outer tube 102. This means that the inner tube 104 and at least a substantial portion of the capturing tool 103 are disposed inside of the bore of the outer tube 102 and shielded from the exterior environment. The capturing tool 103 in particular is in a collapsed or contracted state such that it fits within the bore of the outer tube 102. In some embodiments, the catheter device 100 may be configured such that initially a distal section of the capturing device 103 is disposed outside the outer tube 102 while a proximal section of the capturing device 103 is disposed inside the outer tube 102, and the capturing tool 103 is in the collapsed state.

The outer tube 102 is designed to be retracted and advanced relative to the inner tube 104 via the rotatable fixture 110. For example, the outer tube 102 is retractable relative to the inner tube 104 (i.e., in a proximal direction of the handle) so as to expose the capturing tool 103 in its entirety and a distal portion of the inner tube 104. The outer tube 102 can also be advanced or pushed forward (i.e., in a distal direction away from the handle) to re-cover/conceal the capturing tool 103 and inner tube 104. In some embodiments, after the capturing tool 103 has trapped an object present within the body passage, the outer tube 102 may be configured to advance in a distal direction to cover the capturing tool 103 along with the trapped object. To accommodate the trapped object, the dimensions (e.g., outer diameter) of the inner tube 104 and the dimensions (e.g., inner diameter) of the outer tube 102 may be set so that the space defined therebetween allows for the trapped object to fit within the space. This may be achieved by having the outer tube 102 and/or the inner tube 104 be releasably connected to the handle 101 to enable exchange/replacement, thereby allowing the catheter device to be equipped with any one of a plurality of inner tubes having varying dimensions and/or any one of a plurality of outer tubes having varying dimensions.

Figure 2:
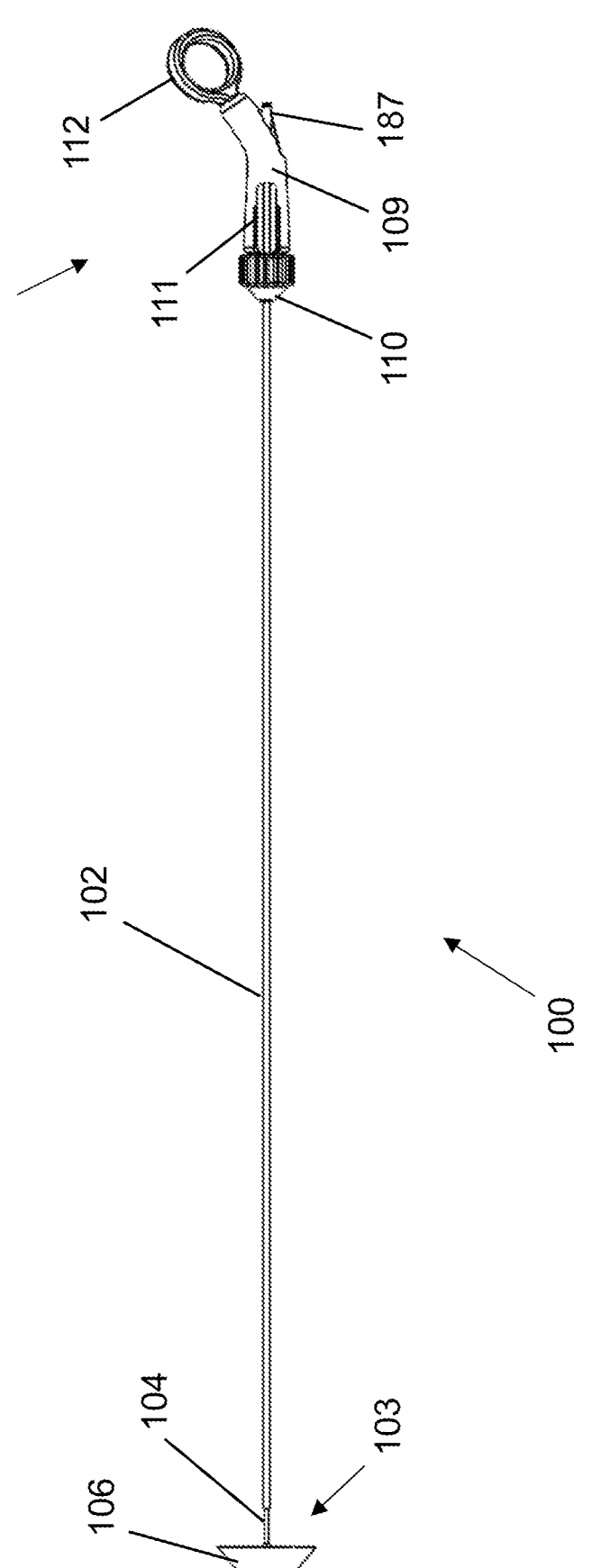
FIG. 2 is a side view of the catheter device of FIG. 1, wherein the capturing tool is exposed outside the outer tube and is placed in an open position.

Referring to FIG. 2, the catheter 100 is shown in an expanded state. In the expanded state, the capturing tool 103 is exposed or unsheathe from within the outer tube 102 and has entered an open or expanded position. The capturing tool 103 is mounted to a distal end of an inner tube 104. In some embodiments, the capturing tool 103 is mounted by means of a releasable connection, which allows for detachment of capturing tool 103 from the inner tube 104. The releasable connection allows for easy replacement of the capturing tool with a new (e.g., clean) capturing tool or another (e.g., different) capturing tool. In other embodiments, the capturing tool 103 may be permanently connected (e.g., welded) to the distal end of the inner tube 104. In addition, the inner tube 104 and/or outer tube 102 may be removable from the catheter handle 101 as described above. These features allow for the catheter device to be adapted to the requirements of a medical procedure, as well as promotes easy cleaning and quick turnaround of the device between consecutive medical procedures.

The inner tube 104 and outer tube 102 are shaped such that they can be inserted into a body passage including, but not limited to, a vein, artery, urethra, lymph duct, airway, vessel, duct, or any other body passage known in the art. One or both of the tubes 102, 104 can each be entirely flexible, entirely rigid, or have sections that are rigid and others that are flexible. The diameter and length of the catheter can vary depending on how wide the body passage into which the tubes 102, 104 must be inserted is and how far they must be inserted to reach the target object (i.e., object to be captured). The inner tube 104 and outer tube 102 can both be manufactured from materials including, but not limited to, polymer, plastic, rubber, metal, composite, or any other material known in the art for constructing medical instruments. Further examples of materials that can be used to construct the inner tube 104 and outer tube 102 include, but are not limited to, silicone rubber, polyurethane, polycarbonate, polypropylene, polyethylene, polyester, polystyrene, PVC, polyethersulfone, thermoplastic elastomers, fluoropolymers, Makolon®, Bayfol®, peek, acrylic, stainless steel, titanium, polylactic acid, and any other material known in the art for producing medical instruments and devices.

Figure 3A:
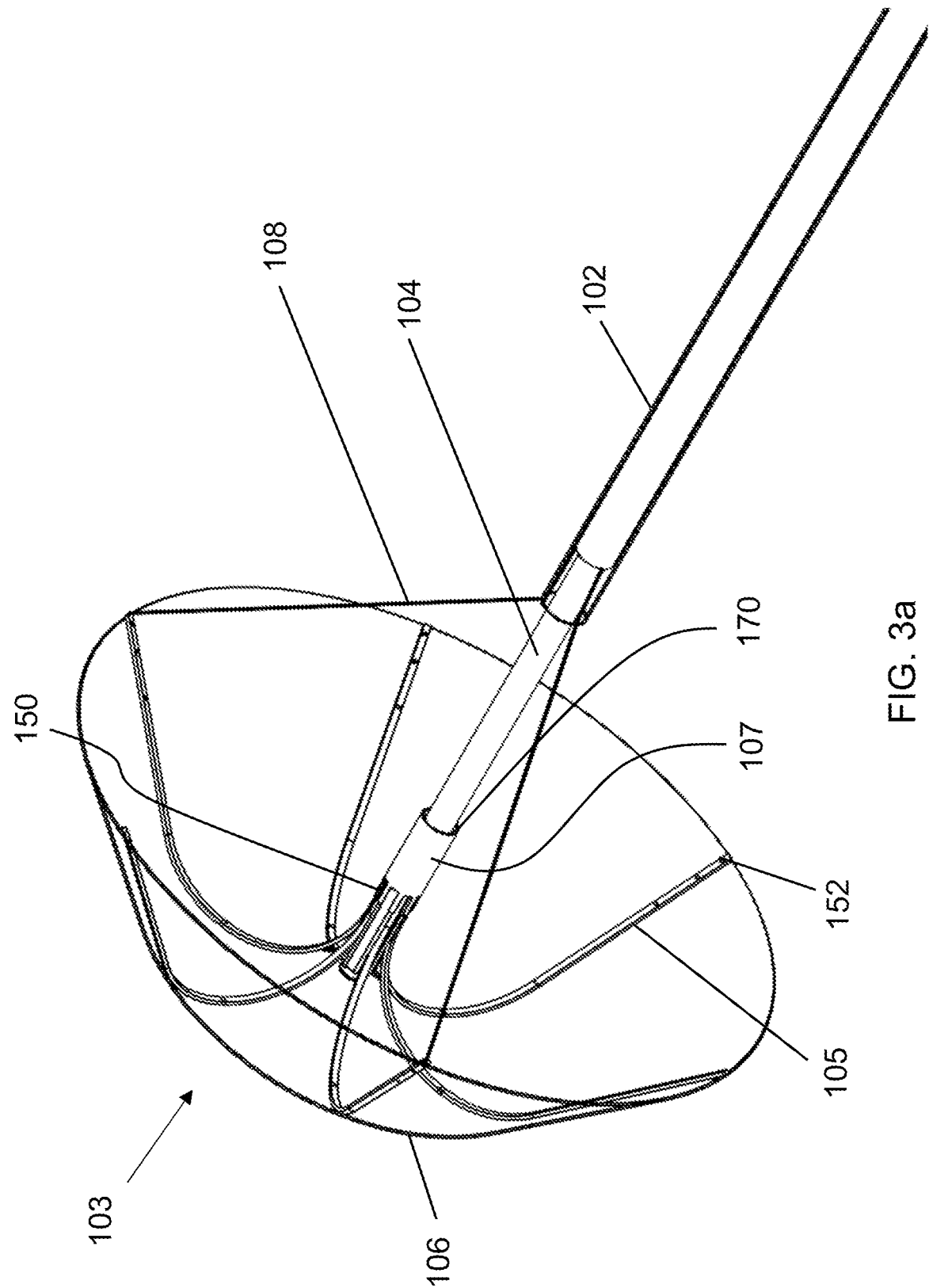
FIG. 3*a* is a perspective view of the capturing tool of the catheter device of FIG. 2, wherein the capturing tool has two drivers that extend away from each other and are connected to the ribs.
Figure 3B:
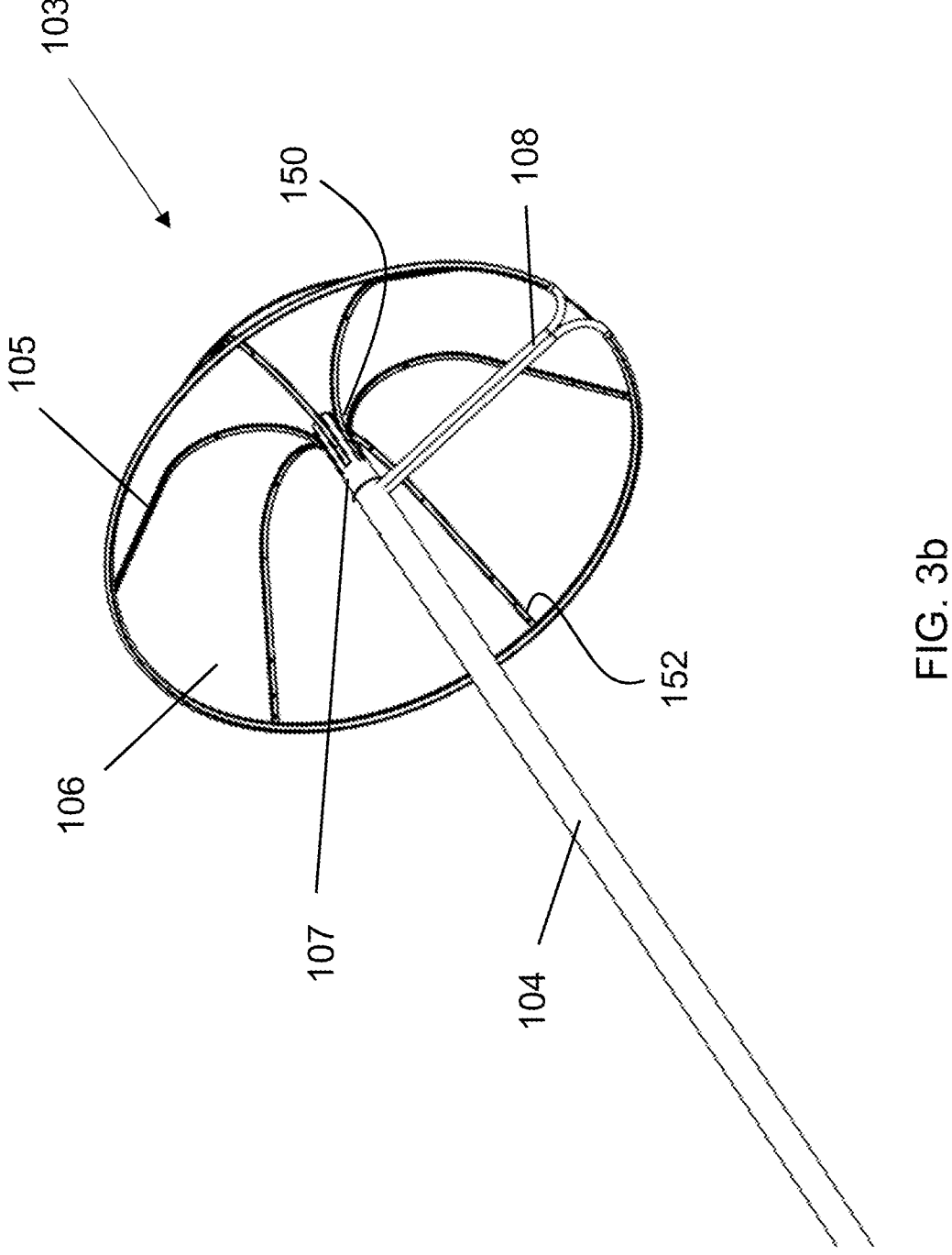
FIG. 3*b* is a perspective view of the capturing tool of the catheter device of FIG. 2, wherein the capturing tool has a driver with two portions that are arranged parallel to each other and form a loop connected to the ribs.

FIGS. 3*a* and 3*b* show perspective views of the capturing tool 103 in its open or expanded position. The capturing tool 103 may have a plurality of ribs 105, a mesh 106 wrapped around the exterior sides of the ribs, and a fitting 107 to which the ribs are connected. Note, FIGS. 3*a*-3*b* depict the mesh 106 in transparent form for ease in illustrating other elements of the catheter device. The mesh 106 may be made of a medical or surgical grade material. In some embodiments, the mesh 106 may be made of an elastomer, so that it can stretch and bend when the capturing tool 103 transitions from the closed/collapsed position to the open/expanded position and it can recover its initial state and/or shape when the capturing tool 103 transitions back to the closed/collapsed state. The mesh 106 comprises a plurality of filaments or fibers that are woven or knitted together to form a web or net with holes/openings/gaps. The filaments may have a plain weave pattern, twill weave pattern, a stain weave pattern, a basket weave pattern, or a leno weave pattern. The mesh 106 can be partially made up of rigid filaments and partially of flexible filaments. The ratio of rigid to flexible filaments can be set based upon the desired collapsed and expanded shapes of the rib 105 and mesh 106 assembly.

The holes/openings/gaps allow for fluids and objects under a certain size, such as blood or cells, to pass through the mesh uninhibited. The mesh size (hole size) of the mesh 106 can vary depending on the requirements of the medical procedure. Generally, the mesh 106 has a mesh size between 3 (0.265 inches; 6730 microns) and 100 (0.0059 inches; 149 microns). In some embodiments, the mesh size may be between 3 and 50 (0.0117 inches; 297 microns), between 3 and 30 (0.0232 inches; 595 microns), between 3 and 10 (0.0787 inches; 2000 microns), between 30 and 70 (0.0083 inches; 210 microns), or between 50 and 70.

The fitting 107 comprises a substantially longitudinal body with a proximal end that includes an insertion hole 170 adapted to receive the distal end of the inner tube 104. With regards to the embodiments where the capturing tool 103 is releasably connected to the inner tube 104, the wall(s) defining the insertion hole 170 may be constructed with female threads, whereas the distal end of the inner tube 104 is constructed with male threads that screw into the female threads. In other embodiments, the releasable connection between the capturing tool 103 and the inner tube 104 may be achieved by a ball-detent. For example, the wall defining the insertion hole 170 may include a ball protruding inward, while the exterior surface of the inner tube 104 includes a detent having a shape that complements the ball. Alternatively, the wall defining the insertion hole 170 may include the detent, while the exterior surface of the inner tube 104 includes the ball. Still, in other embodiments, the releasable connection between the capturing tool 103 and the inner tube 104 may be achieved by a bayonet connector. Irrespective of the mechanism by which the capturing tool 103 and the inner tube 104 are connected to each other, the insertion hole 170 and the inner tube 104 are dimensioned to mate with one another and provide a snug fit.

The distal end of the fitting 107 may be characterized by a closed, solid tip. Such tip may be designed to assist in guiding the catheter device through the body passage to an area where the target object is located. To minimize any unintended trauma to tissue and/or organs, the distal tip of the fitting 107 may be configured with a rounded surface (e.g., dome, hemispherical) without sharp edges. The closed distal tip of the fitting 107 may be made of a polymer. In other embodiments, the distal end of the fitting 107 may have an access port 113 (see FIG. 5*a*) which extends through the longitudinal body of the fitting and joins the insertion hole to form a channel. Once the capturing tool 103 is installed on the distal end of the inner tube 104 via the fitting 107, the access port 113 forms a continuous channel with the bore of the inner tube 104, thus providing communication therebetween. As will be described in further detail below, a guide wire may be fed through the bore of the inner tube 104 and out the access port 113 to assist in guiding the catheter device through the body passage. In addition, or alternatively, the access port 113 and the bore of the inner tube 104 may provide fluid communication, such as introducing a flow of gas into the body passage (insufflation), introducing a flow of liquid—e.g., a saline solution, antibiotic solution, antiseptic agent, etc.—into the body passage (irrigation), and/or removing fluids from the body passage (suction).

Each rib 105 may be rigid or flexible, or may comprise flexible parts and rigid parts. In some instances, the rib 105 may be composed of multiple extensions that connect end to end by joints. The ribs 105 can be made from materials including, but not limited to, polymer, plastic, rubber, metal, composite, or any other material known in the art for constructing medical instruments. Further examples of materials that can be used to construct the ribs 105 include, but are not limited to, silicone rubber, polyurethane, polycarbonate, polypropylene, polyethylene, polyester, polystyrene, PVC, polyethersulfone, thermoplastic elastomers, fluoropolymers, Makolon®, Bayfol®, peek, acrylic, stainless steel, titanium, polylactic acid, Nitinol®, other shape-memory alloys, and any other material known in the art for producing medical instruments and devices.

The ribs 105, in some embodiments, may be made of shape-memory material (e.g., shape memory alloy), such that they can be deformed and have the ability to return to their pre-deformed shape when a stimulus (e.g., heat) is applied. In other embodiments, the ribs may be made of an elastomer, such that they deform as a result of a deforming force applied thereto and are configured to return to their pre-deformed shape when the force ceases or is removed. The capturing tool 103 may comprise at least three ribs 105. For example, the total number of ribs 105 may be four. FIG. 3a shows an embodiment of the capturing tool 103 having six ribs. However, in some embodiments, the capturing tool 103 has only two ribs 105 connected to the fitting 107. The ribs 105 may be attached to the fitting 107 is an equally distributed arrangement. In particular, the ribs 105, as shown in FIG. 3a, are distributed equidistant around the circumference of the fitting 107 and thus are positioned equidistant around the inner tube 104, at 60° increments. However, in different embodiments, the ribs may be arranged asymmetrically or at unequal distances from one another. For instance, the six ribs may be divided into two groups, wherein each group comprises three ribs that are separated from each other by 30°, and wherein one rib of the first group and a neighboring rib of the second group are separated by 120°.

The ribs 105 generally extend radially outward from the fitting 107 when in an open or expanded position. Each rib 105 is curved in an arch-shape, as shown in FIGS. 3a-3b. That is, each rib 105 has a generally parabolic shape, extending in a generally distal direction (e.g., in a direction away from the handle 101) from a first end 150 at the fitting 107, before curving back in towards a generally proximal direction and terminating at a second end 152, which is not directly connected to the inner tube 104. In other embodiments, the ribs 105 may be substantially linear in shape. Irrespective of their shape, the mesh 106 is attached to the ribs 105 at least at their second ends 152. When the ribs 105 are adjusted into the open or expanded position, the mesh 106 is spread out and an underside of the mesh 106 is supported by the ribs 105, thereby shaping the mesh into a canopy resembling an umbrella. In some embodiments, each rib 105 may have multiple fasteners or attachment points along its length that connect to the underside of the mesh 106. The multiple fasteners further stabilize the mesh during use of the catheter device, especially when the mesh is in the open or expanded position. As shown in FIGS. 3a and 3b, when the capturing tool 103 is in the open/expanded position, the ribs 105 and the mesh 106 are configured to form a canopy having circular opening (i.e., the edge(s) of the mesh are arranged in a circle). Alternatively, when the capturing tool 103 is in the open/expanded position, the ribs 105 and the mesh 106 are configured to form a canopy having an oval opening (i.e., the edge(s) of the mesh are arranged in an elliptical shape). The oval opening can be achieved by constructing some of the ribs 105 to have different lengths and/or curvatures compared to the remaining ribs 105, and/or orienting the ribs 105 relative to the fitting 107 so that their second ends 152 are positioned coplanar in an elliptical fashion when the ribs are fully expanded.

The catheter device 100 further comprises at least two drivers 108. Each driver may comprise, for example, one or more linkages, force transmission rods, push-pull rods, force transmission cables, sutures, or the like. The drivers 108 are configured to transmit force (e.g., push, pull, rotation) between the handle 101 and the capturing tool 103 so that a user can actuate the ribs 105 to bend, rotate, and/or contort through manipulation of control elements of the handle 101 (e.g., first grip member 111, a second grip member 112, and a rotatable fixture 110). In other embodiments, the capturing tool 103 may be actuated by means of only one driver 108 (FIG. 3b). The drivers 108 can be mechanical, electromechanical, pneumatic, hydraulic, or any other method known in the art for manipulating an instrument.

The drivers 108 may extend along the outside of the inner tube 104 and connect the handle 101 to the capturing tool 103. For example, the drivers 108 are disposed in the space defined between the interior surface of the outer tube 102 and the exterior surface of the inner tube 104. The drivers 108 are configured to exert a force on the ribs 105 to move and fix the ribs 105 in a position/orientation relative to the inner tube 104. The drivers 108 may be connected to the second ends 152 of the ribs 105 and the handle 101 such that they are movable in a pulling motion in relation to the inner tube 104 in order to transition the ribs 105 and mesh 106 from the open/expanded position towards the closed/collapsed position. In addition or alternatively, the drivers 108 may be connected to the mesh 106. The drivers 108 can be attached to the ribs 105 and/or mesh 106 by use of connectors including, but not limited to, fasteners, hinges, flexible joints, adhesives, sealants, moldings, pins, slots, soldering, welding, or any other method known in the art for joining materials. In other embodiments, the drivers 108 may be substantially disposed within the bore of the inner tube 104, such that they extend inside the inner tube 104 from the handle 101 towards the distal end of the inner tube 104, wherein the inner tube 104 includes one or more apertures through which the drivers 108 exit and subsequently connect to the ribs 105.

Figure 3C:
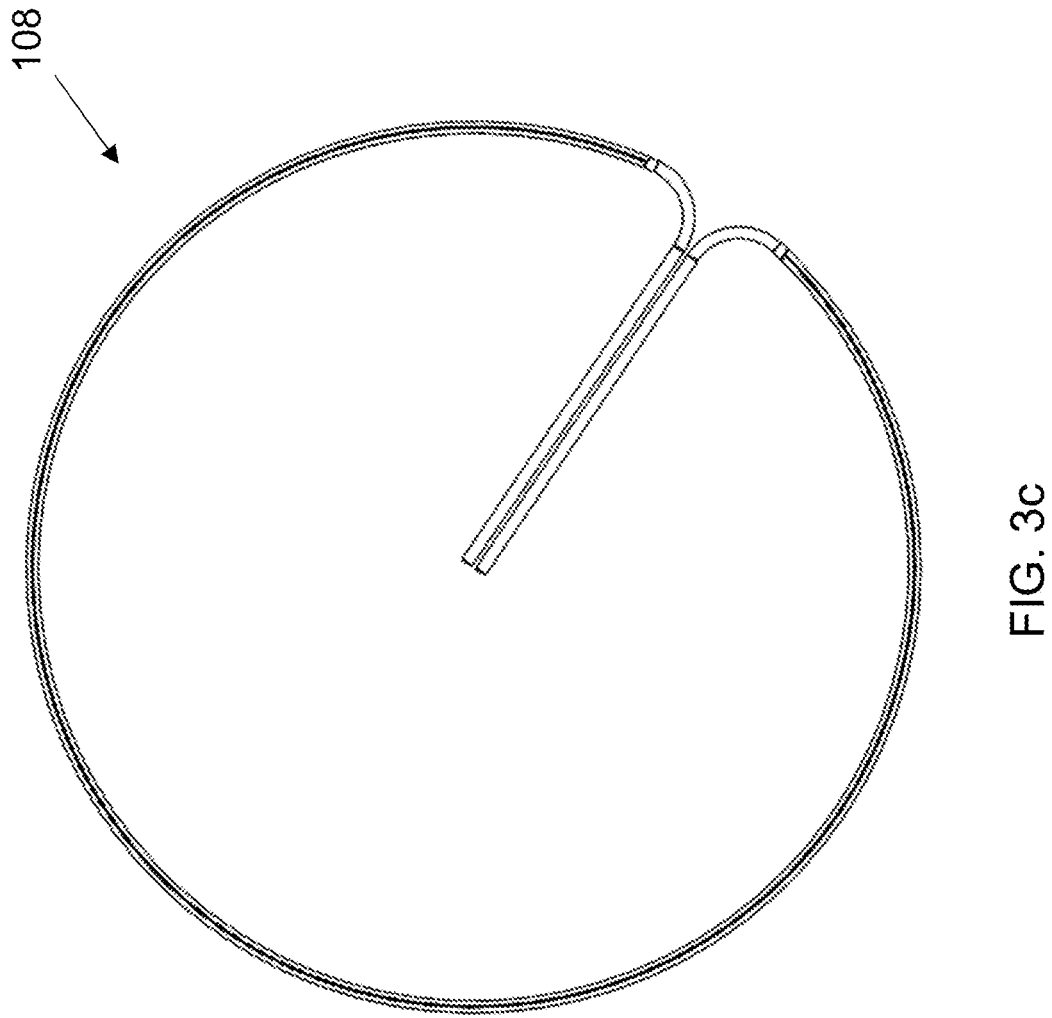
FIG. 3*c* is a front view of the driver of FIG. 3*b*.

As shown in FIG. 3a, one embodiment of the capturing tool 103 can have two drivers 108 (e.g., suture) that extend away from each other and connect to ribs 105 on opposing sides of the fitting 107. In some embodiments, the number of drivers 108 equals the number of ribs 105 in the capturing tool 103, so that there is one driver 108 connected to each rib 105. In other embodiments, the number of drivers 108 equals the number of ribs 105 in the capturing tool 103, so that each driver 108 is connected to the mesh 106 at a point between the adjacent ribs. FIGS. 3b and 3c show another embodiment of the capturing tool 103, wherein two portions of a single driver 108 extend along the inner tube 104 in a direction of the capturing tool 103, the two portions then extend in a radially outward direction from the inner tube 104 parallel with each other, and subsequently connect to the ribs 105. The two portions of the driver may also extend in circumferential directions around a longitudinal axis of the inner tube 104 and form a loop, as shown in FIGS. 3b and 3c. In other embodiments, instead of the two portions of the single driver extending in parallel, they may be arranged colinear and extend in opposite radial directions.

The drivers 108 can be entirely rigid, entirely flexible, or partially flexible and partially flexible. The drivers 108 may each have multiple joints that connect individual sections (e.g., linkages) together. The drivers 108 can be hollow or solid and be made up of one piece or multiple pieces. The drivers 108 may be configured to move proximally and/or distally in relation to the inner tube 104 between an extended position (which corresponds to an open/expanded position of the ribs and mesh) and a retracted position (which corresponds to a closed/collapsed position of the ribs and mesh). For example, the drivers 108 move in a proximal direction towards the handle 101 to arrive at a retracted position. On the other hand, the drivers 108 may move in a distal direction away from the handle 101 to reach an extended position. The extended position of the drivers 108 is depicted in FIGS. 3a and 3b.

The drivers 108 can also move in directions including, but not limited to, moving laterally in a direction parallel to the long direction of the inner tube 104, transition the capturing tool 103 between the expanded/open and collapsed/closed positions. The drivers 108 can be made from materials including, but not limited to, Nitinol®, silicone rubber, polyurethane, polycarbonate, polypropylene, polyethylene, polyester, polystyrene, PVC, polyethersulfone, thermoplastic elastomers, fluoropolymers, Makolon®, Bayfol®, peek, acrylic, stainless steel, titanium, polylactic acid, other shape-memory alloys, and any other material known in the art for producing medical instruments and devices.

Figure 4:
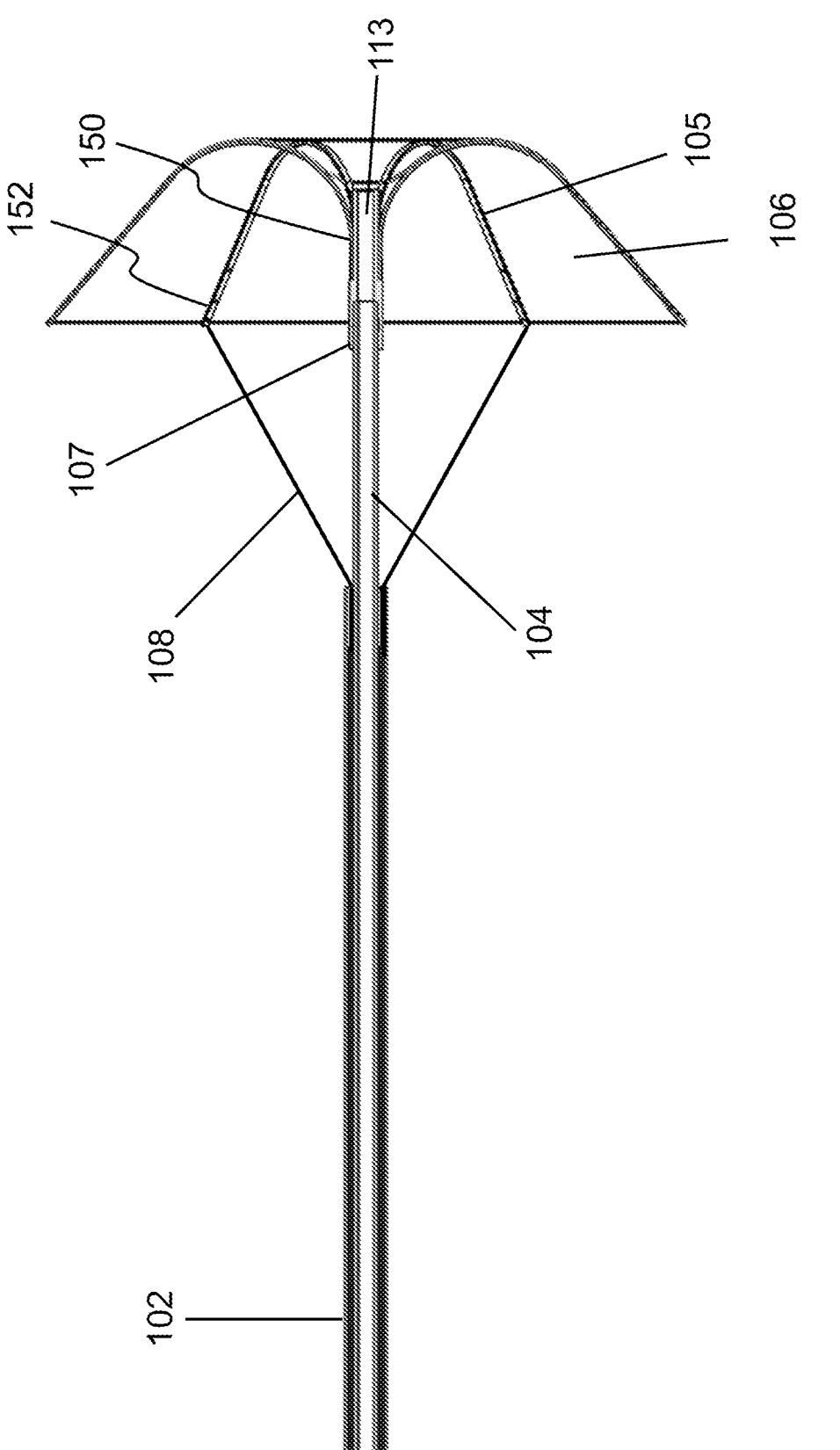
FIG. 4 is a cross-sectional view of the capturing tool of FIG. 3*a*.
Figure 5A:
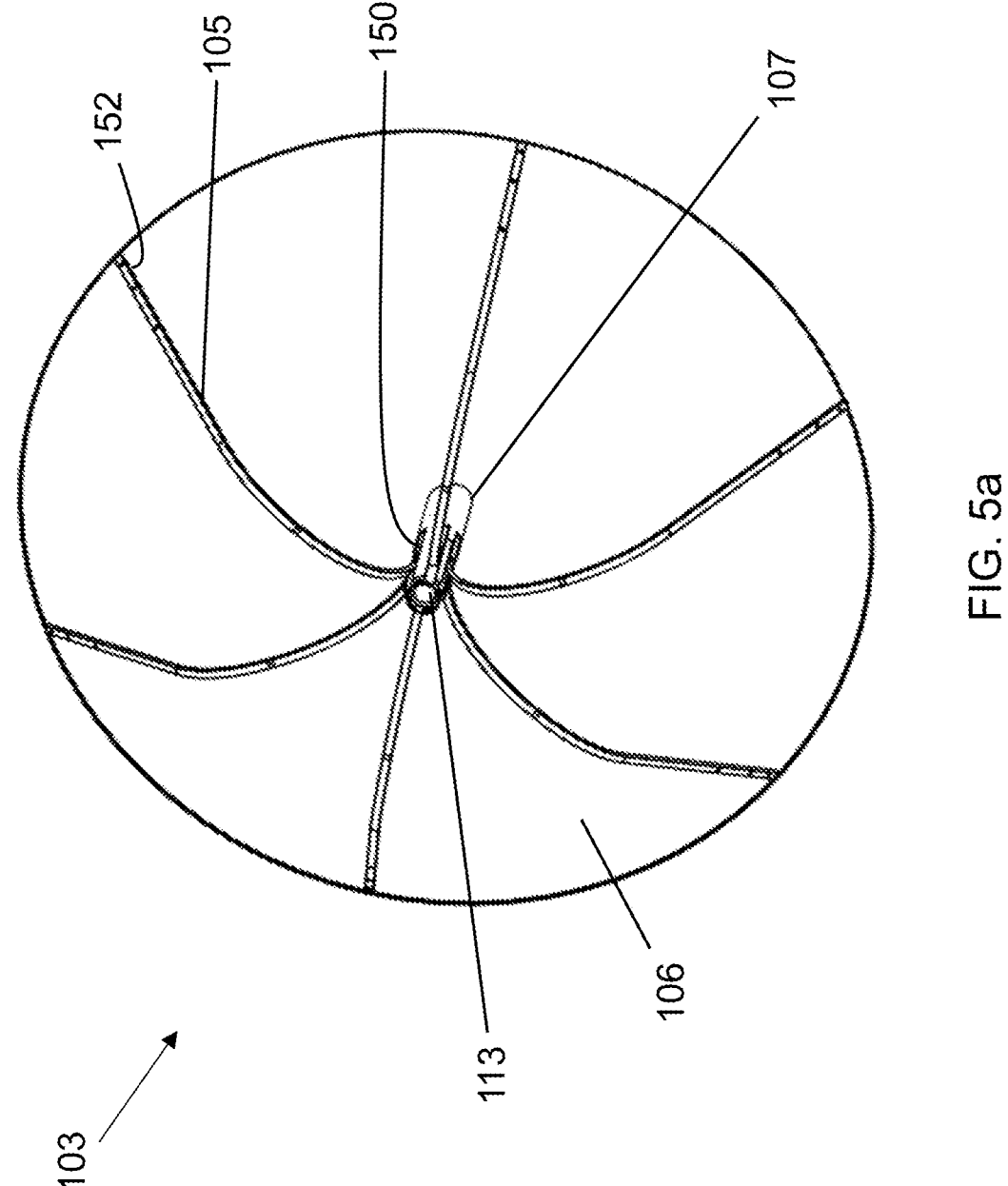
FIG. 5*a* is a perspective view of the capturing tool shown in FIG. 2, which may be releasably attached (i.e., attachable and detachable) to the distal end of an inner tube.
Figure 5B:
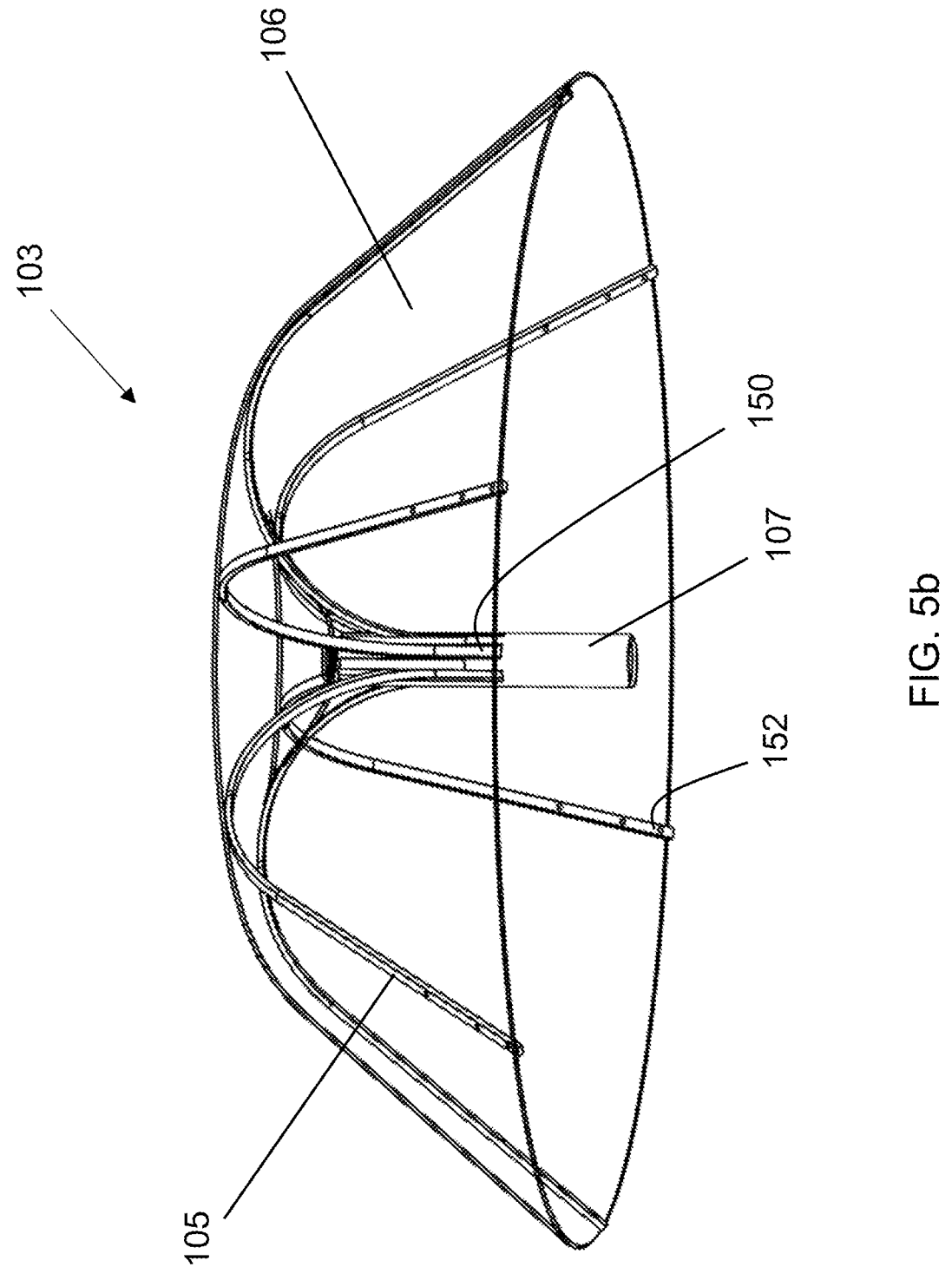
FIG. 5*b* is a side view of the capturing tool shown in FIG. 5*a*.

As illustrated in FIGS. 4, 5a, and 5b, when the capturing tool 103 of the catheter 100 is in the open/expanded position, the ribs 105 extend away from the inner tube 104 and fitting 107. For example, the ribs 105 extend outward from the fitting 107 in an arc shape. The first ends 150 of the ribs 105 are attached at first connection points to the fitting 107. The mesh 106 covers the topside of the ribs 105 and connects to at least the second ends 152 of the ribs 105. When the drivers 108 transmit a force from the handle 101 to the ribs 105 (e.g., pulling force), the second ends 152 of the ribs are shifted (e.g., pulled) towards the fitting 107 and inner tube 104, which in turn collapses or contracts the mesh 106, thereby placing the capturing tool 103 in a closed/collapsed state. The drivers 108 are configured to hold each rib 105 in position adjacent to the fitting 107 and/or the inner tube 104, by tension, compression, or bending forces. In other embodiments, a reverse technique or mechanism is employed by the catheter device. The reverse technique comprises the drivers 108 transmitting a force from the handle 101 to the ribs 105 (e.g., pushing force), the second ends 152 of the ribs are shifted outward away from the fitting 107 and inner tube 104, which in turn opens or expands the mesh 106, thereby placing the capturing tool 103 in an open/expanded state. The drivers 108 are configured to hold each rib 105 in the outward position by tension, compression, or bending forces. Still, in other embodiments, the catheter device 100 may employ both techniques to actuate the capturing tool 103 back and forth between the open/expanded state and the closed/collapsed state.

Referring to FIG. 5b, the capturing tool 103 can have multiple ribs 105 that connect to the fitting 107 of the capturing tool 103. The ribs 105 can move in a hinging motion towards and away from the inner tube 104 in response to force transmitted via the drivers 108. For example, the first connection point where the first end 150 of each rib 105 is connected to the fitting 107 may comprise a hinge having a pivot axis substantially perpendicular to the longitudinal axis of the fitting 107 (and the longitudinal axis of the inner tube 104). In this particular configuration, when the drivers 108 transmit a pulling force from the handle 101 to the ribs 105, the ribs pivot relative to the fitting 107, which enables the second ends 152 of the ribs 105 to move towards the fitting 107 and the inner tube 104 and in turn collapses or contracts the mesh 106, thereby placing the capturing tool 103 in a closed/collapsed state. When the drivers 108 transmit a pushing force from the handle 101 to the ribs 105, the ribs pivot in the opposite direction, which compels the second ends 152 of the ribs 105 to move away from the fitting 107 and the inner tube 104, thereby placing the capturing tool 103 in an open/expanded state. An alternative configuration may involve the inverse interaction between force transmission of the drivers and actuation of the ribs, where a pulling force pivots the ribs into the open/expanded state and a pushing force pivots the ribs into the closed/collapsed state. In yet other embodiments, the first connection point where the first end 150 of each rib 105 is connected to the fitting 107 may comprise a spring-loaded hinge, such that the ribs automatically return to the open/expanded state in the absence of a force (e.g., pulling force) being exerted by the drivers 108, or alternatively, they automatically return to the closed/collapsed state in the absence of a force (e.g., pushing force).

Figure 5C:
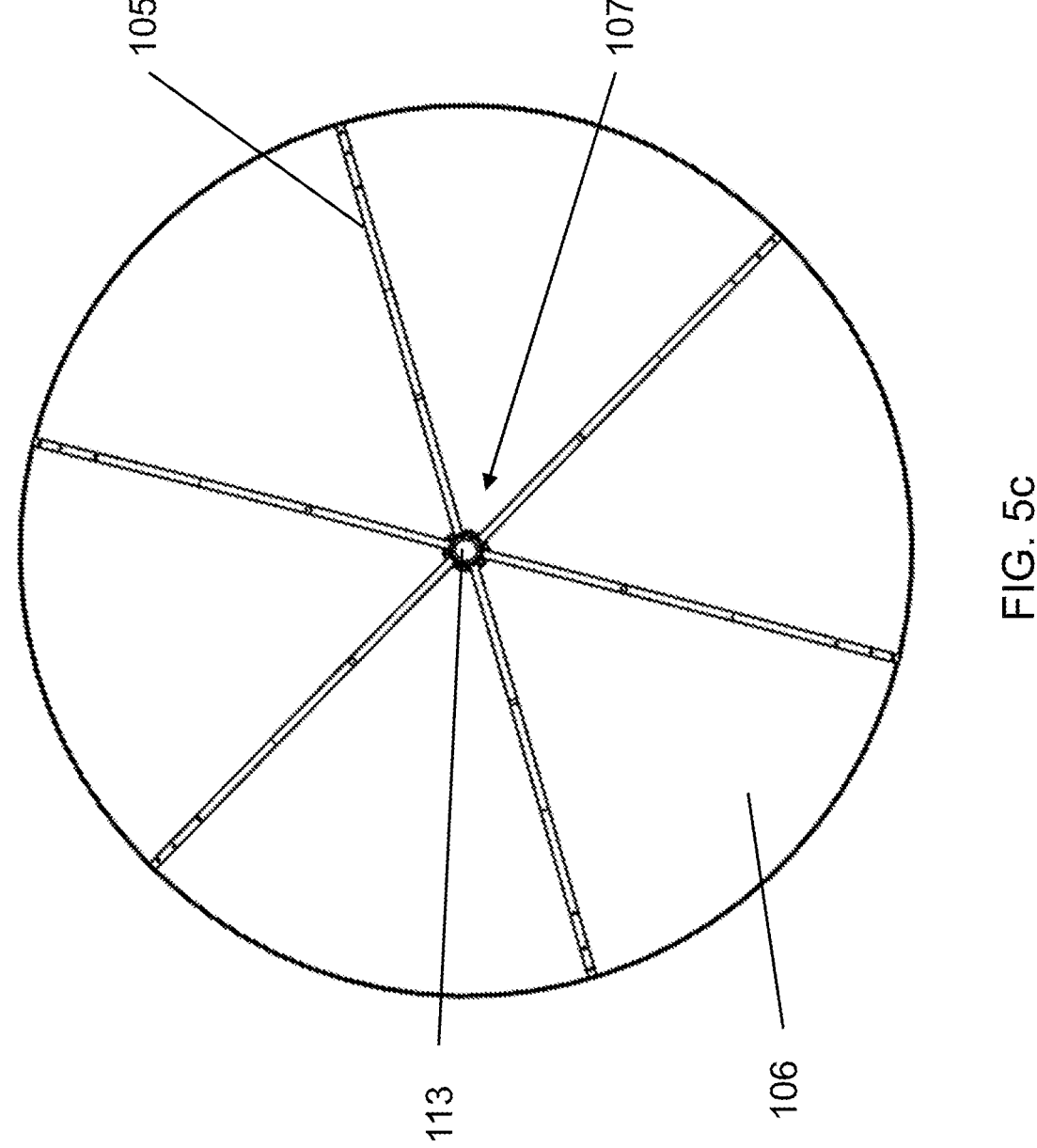
FIG. 5*c* is a front view of the capturing tool shown in FIG. 5*a*.
Figure 5D:
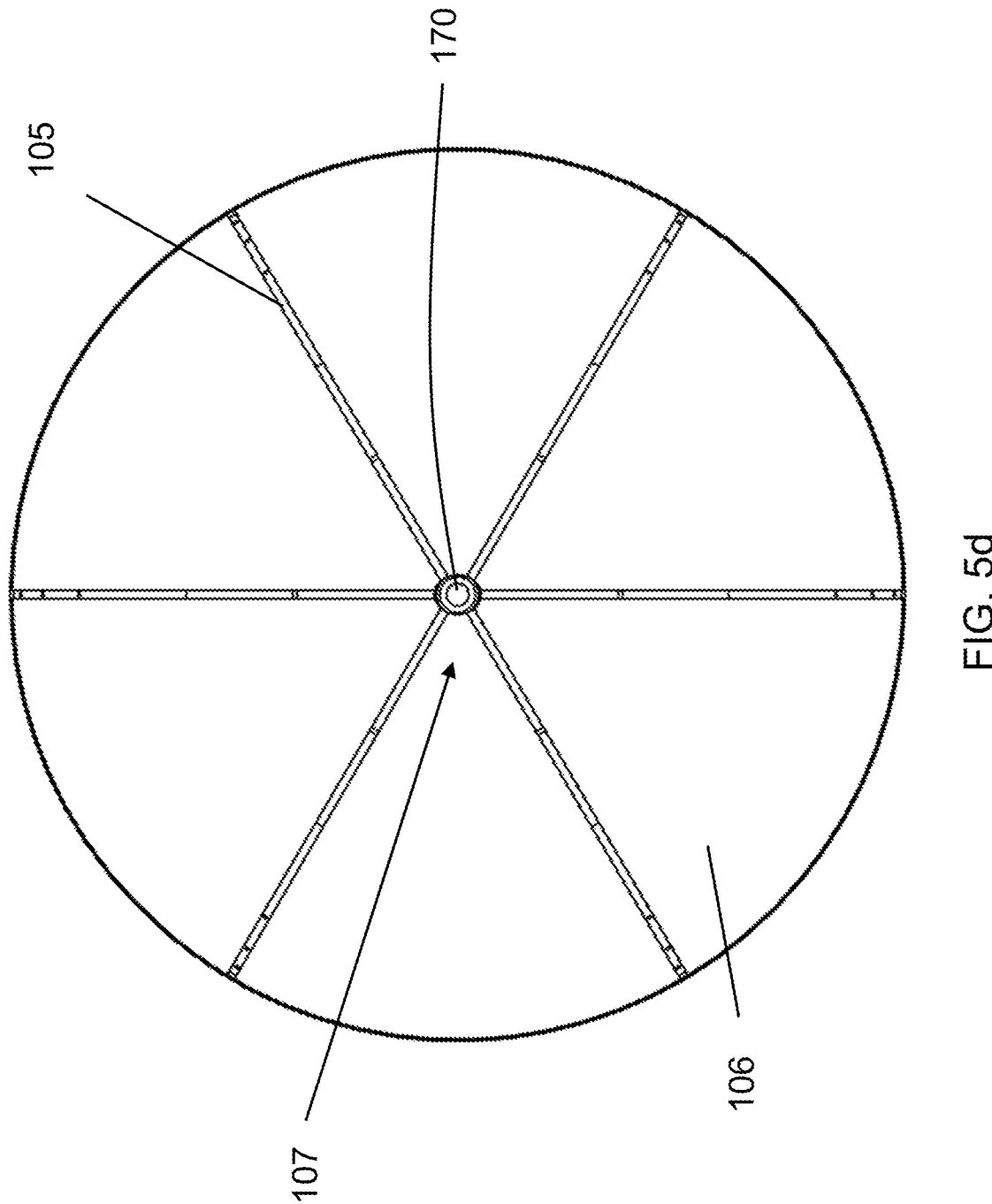
FIG. 5*d* is a rear view of the capturing tool shown in FIG. 5*a*.

FIGS. 5c and 5d respectively show a front view and a review view of the capturing tool 103. The proximal end of the fitting 107 may be configured to include an insertion hole 170 for receiving the distal end of the inner tube 104. The insertion hole 170 is designed to releasably attach to the inner tube 104, thereby allowing for easy detachment and installation. For example, the insertion hole 170 may have with female threads that are engaged with corresponding male threads present on the outer surface of the inner tube 104. In other embodiments, the releasable connection between the capturing tool 103 and the inner tube 104 may be achieved by a ball-detent. Still, in other embodiments, the releasable connection between the capturing tool 103 and the inner tube 104 may be achieved by a bayonet connector. Irrespective of the mechanism by which the capturing tool 103 and the inner tube 104 are connected to each other, the insertion hole 170 and the inner tube 104 are dimensioned to mate with one another and provide a snug fit. The distal end of the fitting 107 may be configured to include an access port 113. The port 113 extends through the longitudinal body of the fitting 107 and joins the insertion hole 170 to form a channel. Accordingly, the access port 113 provides for communication from the bore of the inner tube 104, through the fitting 107, and out of the distal end of the fitting 107. A guide wire, for example, may be fed through the bore of the inner tube 104 and out the access port 113 to assist in guiding the catheter device through the body passage. In addition, or alternatively, the access port 113 and the bore of the inner tube 104 may provide fluid communication, such as introducing a flow of gas into the body passage (insufflation), introducing a flow of liquid—e.g., a saline solution, antibiotic solution, antiseptic agent, etc.—into the body passage (irrigation), and/or removing fluids from the body passage (suction). In order to provide uninhibited passage to and from the access port 113, the mesh 106 may be configured to include an aperture at its center (corresponding to the longitudinal axis of the fitting 107). The edges of the aperture may be attached to the sides of the fitting 107 to provide further stability to the mesh 106.

Figure 6A:
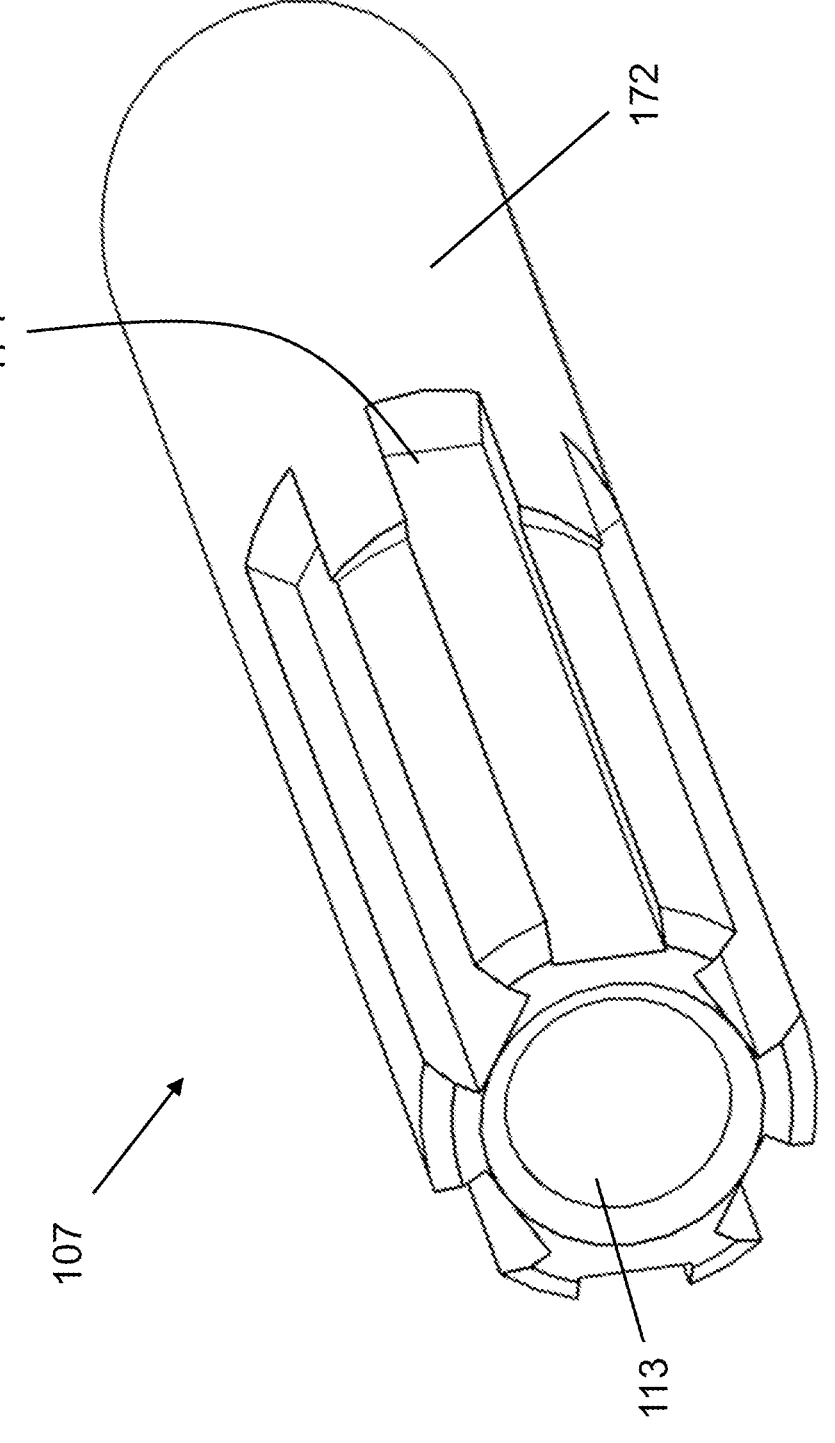
FIG. 6*a* is a perspective view of one embodiment of the capturing tool fitting of FIGS. 3*a*-3*b*.
Figure 6B:
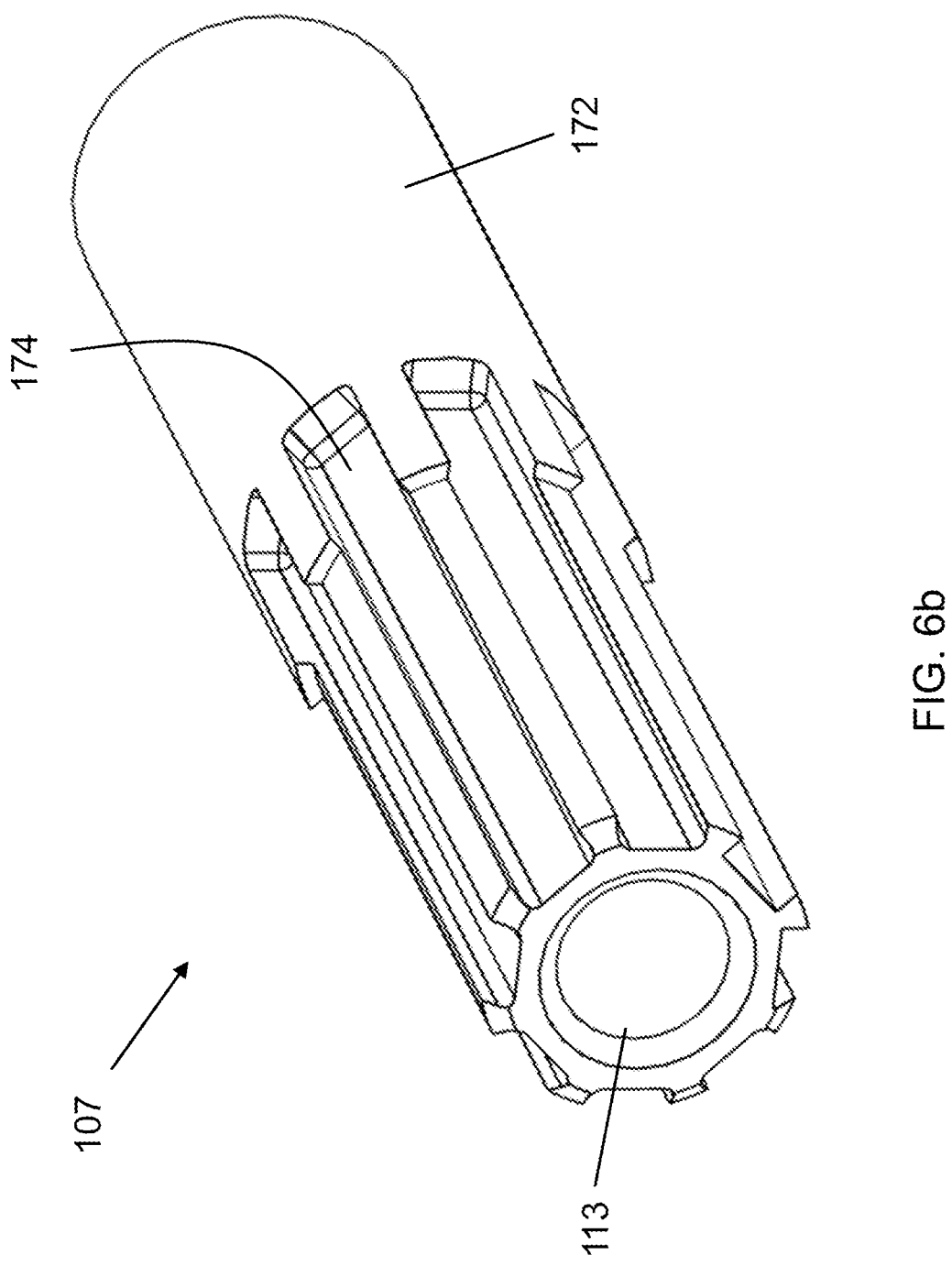
FIG. 6*b* is a perspective view of another embodiment of the capturing tool fitting shown in FIGS. 3*a*-3*b*.

As illustrated in FIGS. 6a and 6b, the fitting 107 comprises a body 172, through which the access port 113 and the insertion hole 170 are formed. The exterior surface of the body 172 may comprise a plurality of recesses, slots, or channels 174 that are designed to receive the first ends 150 of the ribs 105. More specifically, the recesses, slots, or channels 174 constitute the first connection points where the first ends 152 of the ribs 105 are connected (e.g., releasably connected) to the fitting 107. As shown in FIGS. 6*a* and 6*b*, the recesses, slots, or channels 174 start at the distal end of the fitting 107 and extend longitudinally to a proximal section of the fitting 107. In some embodiments, the recesses, slots, or channels 174 may be designed to provide slot-tab connections, where the first ends 150 of the ribs 105 would constitute the tabs. In other embodiments, the recesses, slots, or channels 174 and the first ends 150 of the ribs 105 form a dovetail joint (e.g., sliding dovetail), wherein the ribs are configured to slide into the recesses, slots, or channels 174. The fitting of FIG. 6*a* includes six slots 174 for receiving six ribs 105, whereas the fitting of FIG. 6*b* includes eight slots 174 for receiving six ribs 105.

Figure 7A:
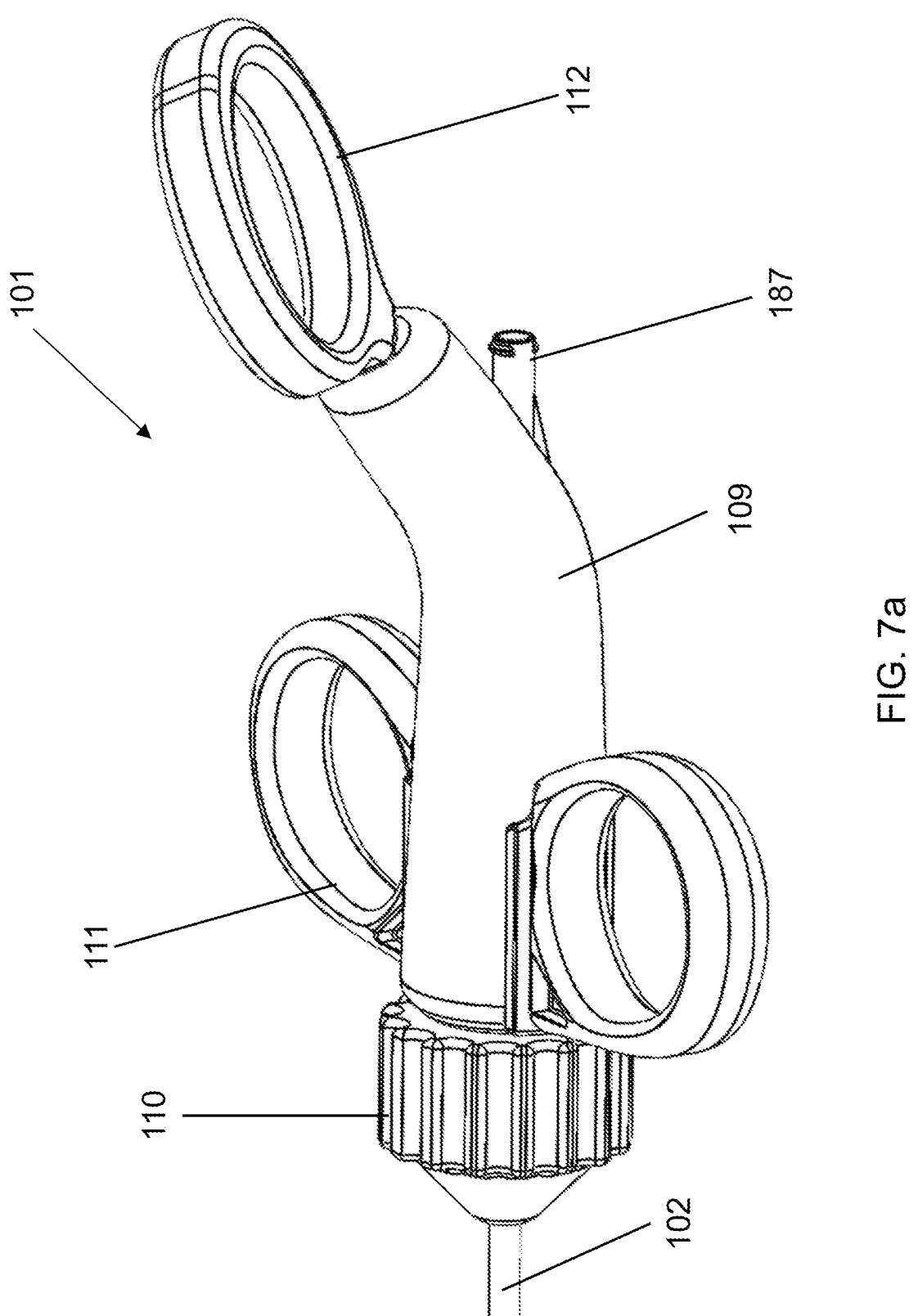
FIG. 7*a* is a side perspective view of the handle of the catheter device of FIG. 1.
Figure 7B:
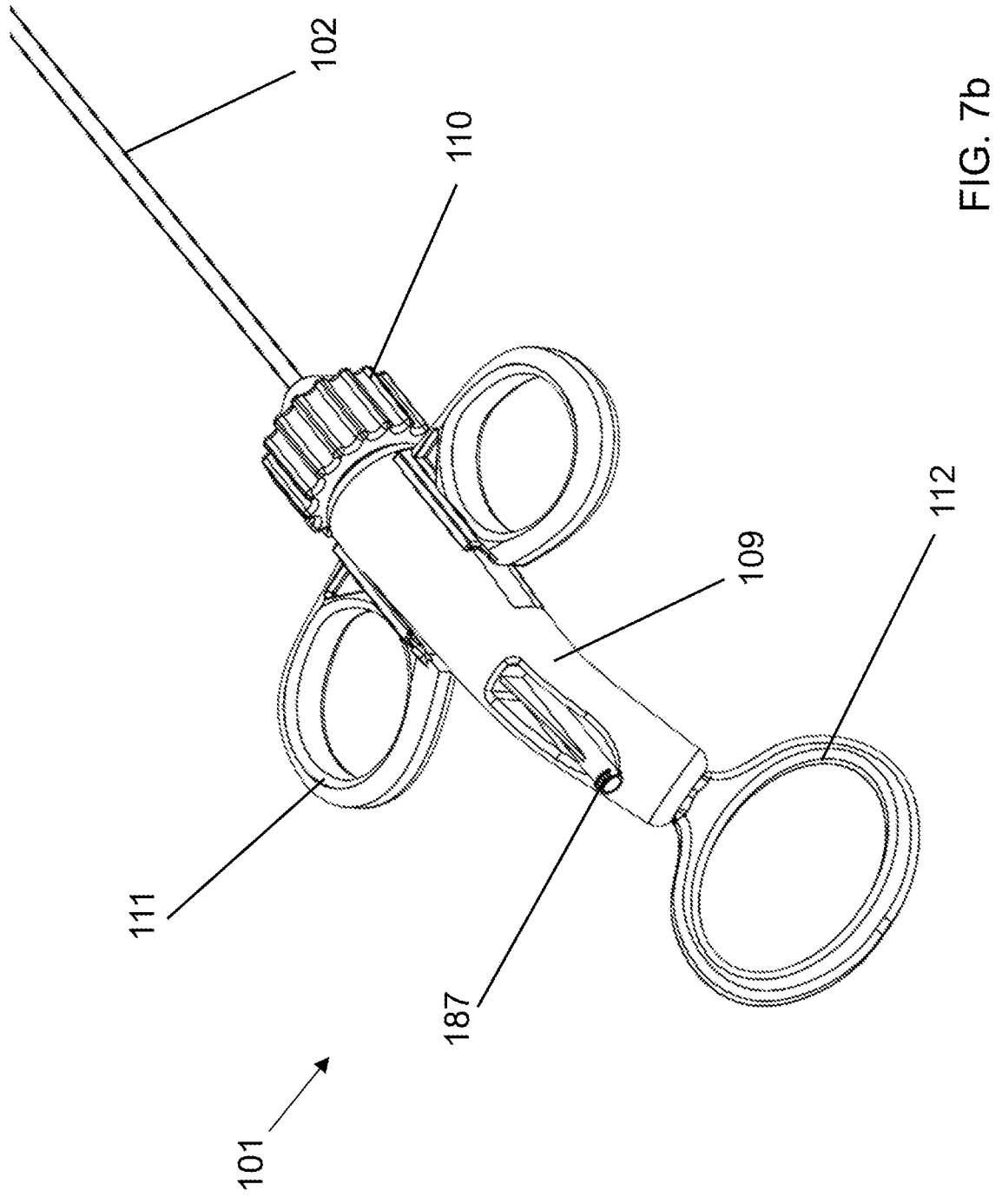
FIG. 7b is an end perspective view of the handle of the catheter device of FIG. 1.

Referring to FIGS. 7*a* and 7*b*, the handle 101 has a base 109, a rotatable fixture 110 disposed at the distal end of the base 109, a first grip member 111 disposed along a distal section of the base 109, a second grip member 112 disposed at a proximal end of the base 109, and an access port 113. The rotatable fixture 110 includes an interior channel within which a proximal section of the outer tube 102 is positioned. The rotatable fixture 110 is configured to actuate movement of the outer tube 102 relative to the inner tube 104. For example, the rotatable fixture 110 can be turned clockwise (or counter-clockwise) to retract the outer tube 102 in a proximal direction. In doing so, the proximal end of the outer tube 102 may shift further into the base 109. Also, the capturing tool 103 and at least the distal end of the inner tube 104 become exposed. In the embodiments where the ribs 105 are elastomeric or are spring-loaded at the first connection points, the ribs may be predisposed to expand into the open/expanded state (pre-deformed shape of an umbrella), such that they automatically transition to the open/expanded state when the outer tube 102 no longer surrounds the capturing tool 103. Prior to retracting the outer tube 102 relative to the inner tube 104 and exposing the capturing tool 103, the outer tube 102 inhibits the outward expansion of the ribs 105. The rotatable fixture 110 can be turned counter-clockwise (or clockwise) in order to advance the outer tube 102 relative to the inner tube 104 in a distal direction. For instance, after the mesh 106 has captured or netted an object within the body passage and the ribs 105 have been actuated back into the closed/collapsed state to trap the object, the outer tube 102 may be advanced in the distal direction, thereby enveloping the capturing tool 103 as well the object within the space defined between the exterior surface of the inner tube 104 and the interior surface of the outer tube 102. An exemplary mechanism for retracting and advancing the outer tube 102 relative to the inner tube 104 may involve threads on the exterior surface of the outer tube 102 and threads in the interior channel of the rotatable fixture 110 that engage the outer tube threads. In some embodiments, the rotatable fixture 110 is a knob.

Figure 8A:
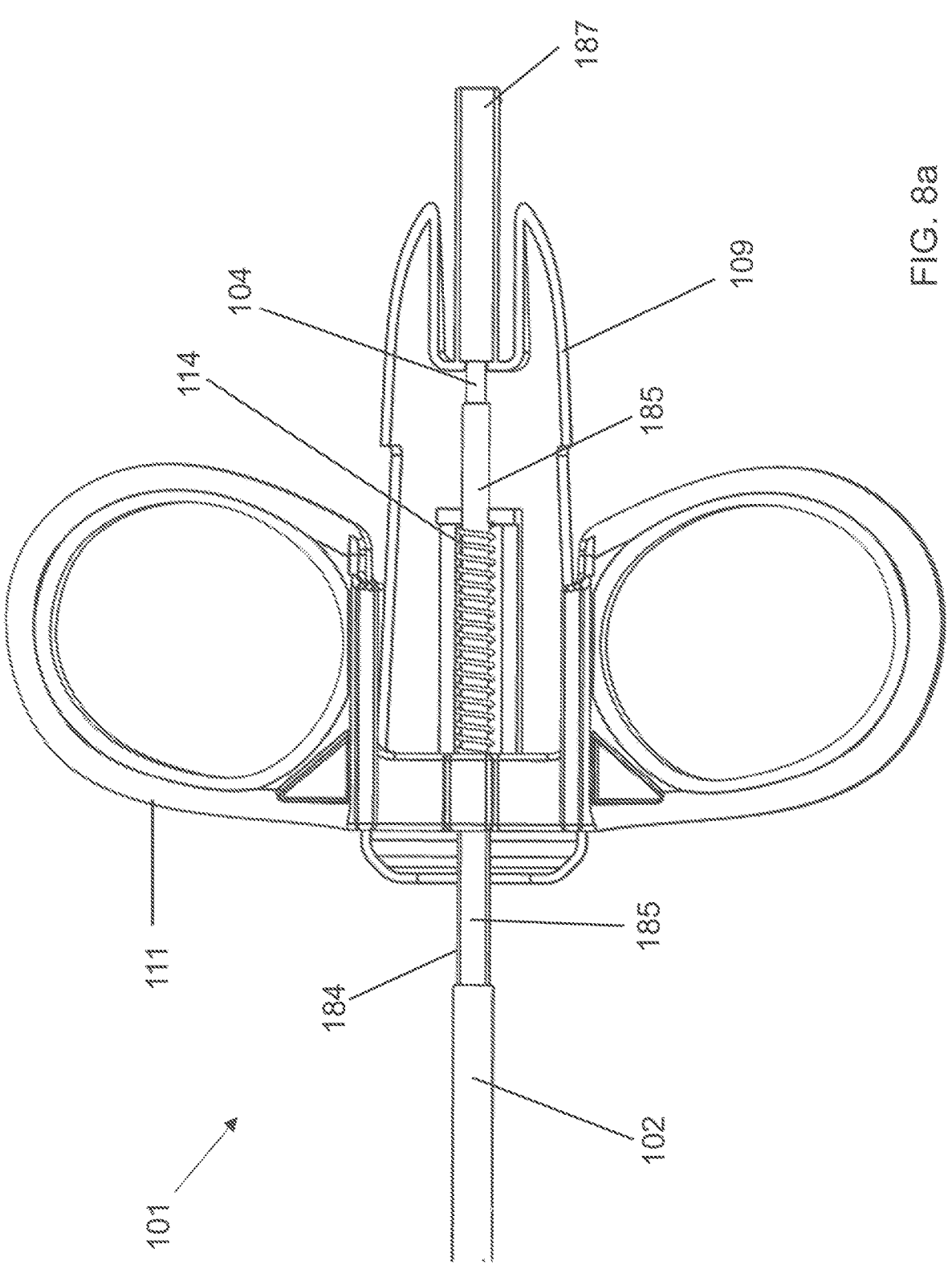
FIG. 8a is a cross-sectional view of the handle shown in FIGS. 7a-7b.

As shown in FIGS. 7*a* and 7*b*, the first grip member 111 is located proximally relative to the rotatable fixture 110. The first grip member 111 may comprise two finger loops, adapted to receive two fingers of the user, preferably the index finger and middle finger. FIG. 8*a* shows that the first grip member 111, which extends through the handle base 109, is configured to be connected to the drivers 108 in order to transmit a force. The first grip member 111 can be configured as a slide (sliding mechanism designed to provide translational movement) and shaped such that when the first grip member 111 is pressed in the proximal direction of the catheter 100, the ribs 105 are actuated (e.g., collapsed) toward the inner tube 104. The second grip member 112 is at the proximal end of the base 109 and actuates with the base 109 for ergonomic support.

The first grip member 111 and the second grip member 112 can be positioned such that a user only needs to use one hand to actuate the catheter 100. For example, a user may hold the base 109 such that the user's index finger and middle finger rest on the first grip member 111 and the user's thumb rests on the second grip member 112. To actuate the capturing tool 103, the user presses on the first grip member 111 with the above referenced fingers, pulling the first grip member 111 in a proximal direction.

In FIG. 7*b*, a tube port 187 extends out from a proximal section of the base 109 and is connected to the proximal end of the inner tube 104. The tube port 113 thus forms a continuous channel with the bore of the inner channel 104, all the way to the access port 113 of the fitting 117 of the capturing tool 103. The tube port 187 is hollow to allow for the insertion of a medical instrument used in the field (e.g., endoscope). A distal end of the medical instrument can subsequently extend out through the access port 113 from the distal end of the catheter device 100. In some embodiments, the first grip member 111 (e.g., slide) may have finger loops on each side of the base 109, and the second grip member 112 may have a finger loop primarily designed to accept a thumb. A cap (not shown) may be inserted into the tube port 187 to provide a closed seal.

Figure 8B:
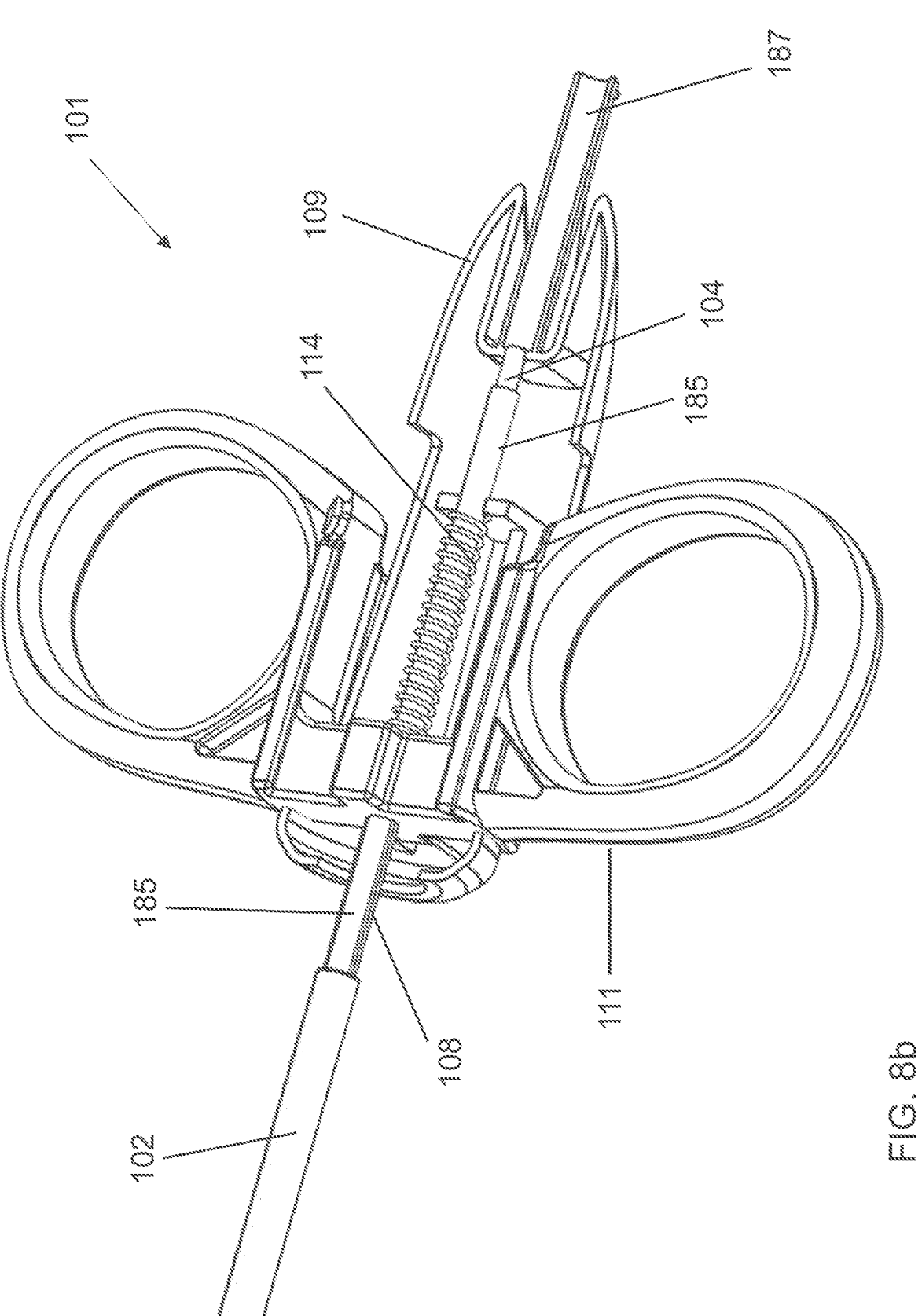
FIG. 8b is a perspective cross-sectional view of the handle shown in FIGS. 7a-7b.

As illustrated in FIGS. 8*a*-8*b*, the base 109 can have a spring 114 that acts to resist movement of the first grip member 111 and, upon the removal of proximal-direction force on the first grip member 111, the spring 114 moves the first grip member 111 toward a distal resting position. The distal resting position of the first grip member 111 can correspond with the expanded position of the capturing tool 103 depicted in FIG. 2. The spring 114 can be made from materials including, plastic, polymer, rubber, metal, elastomer, composite, or any other material known in the art for making springs and medical devices. The spring 114 can be a coil, wave, compressible elastomer sleeve, leaf, or any other design of spring known in the art.

Figure 9A:
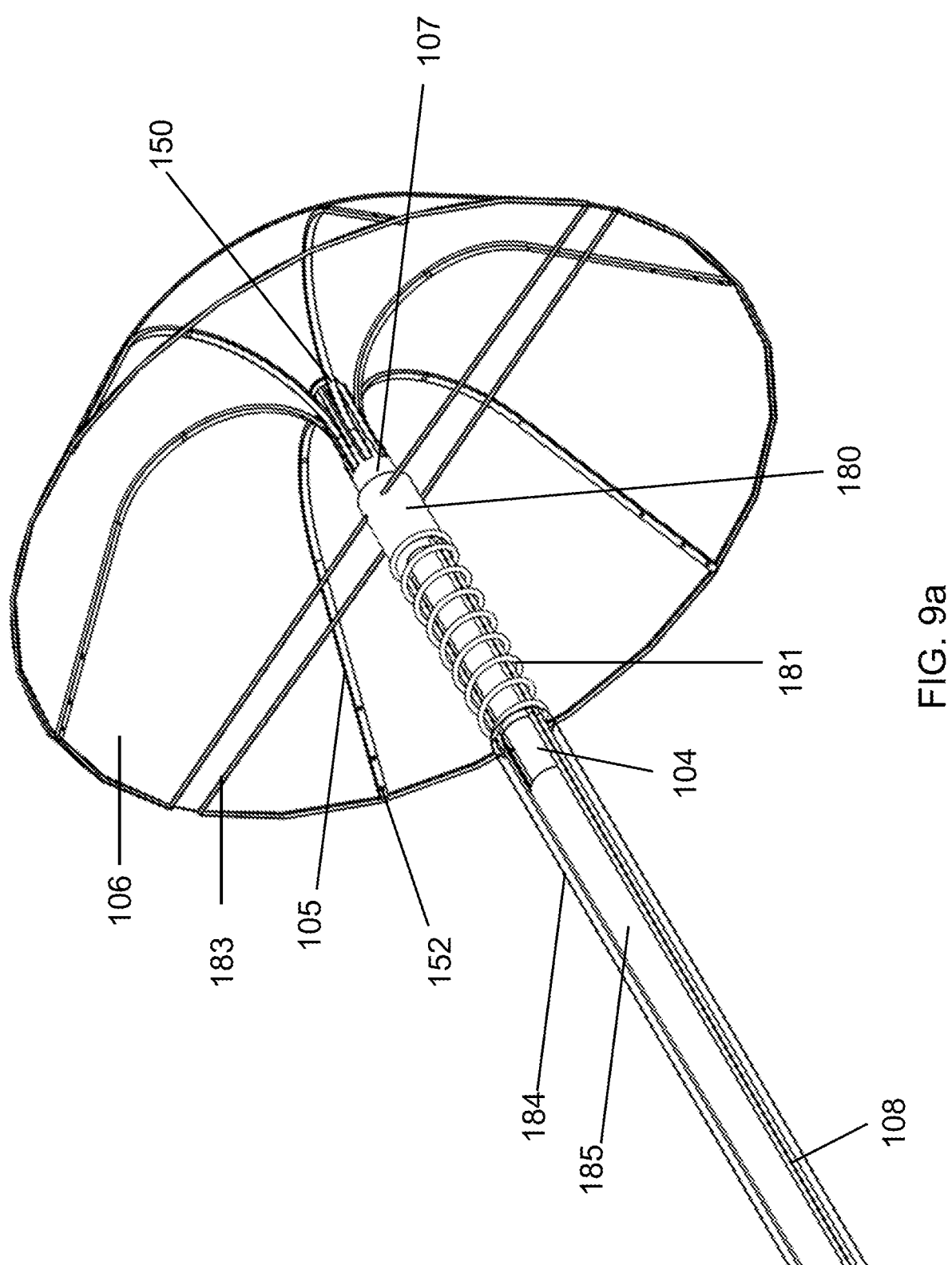
FIG. 9a is a perspective view of another embodiment of the capturing tool of the catheter device of FIG. 2, wherein the capturing tool ribs are connected to a spring guide via guide wires.
Figure 9B:
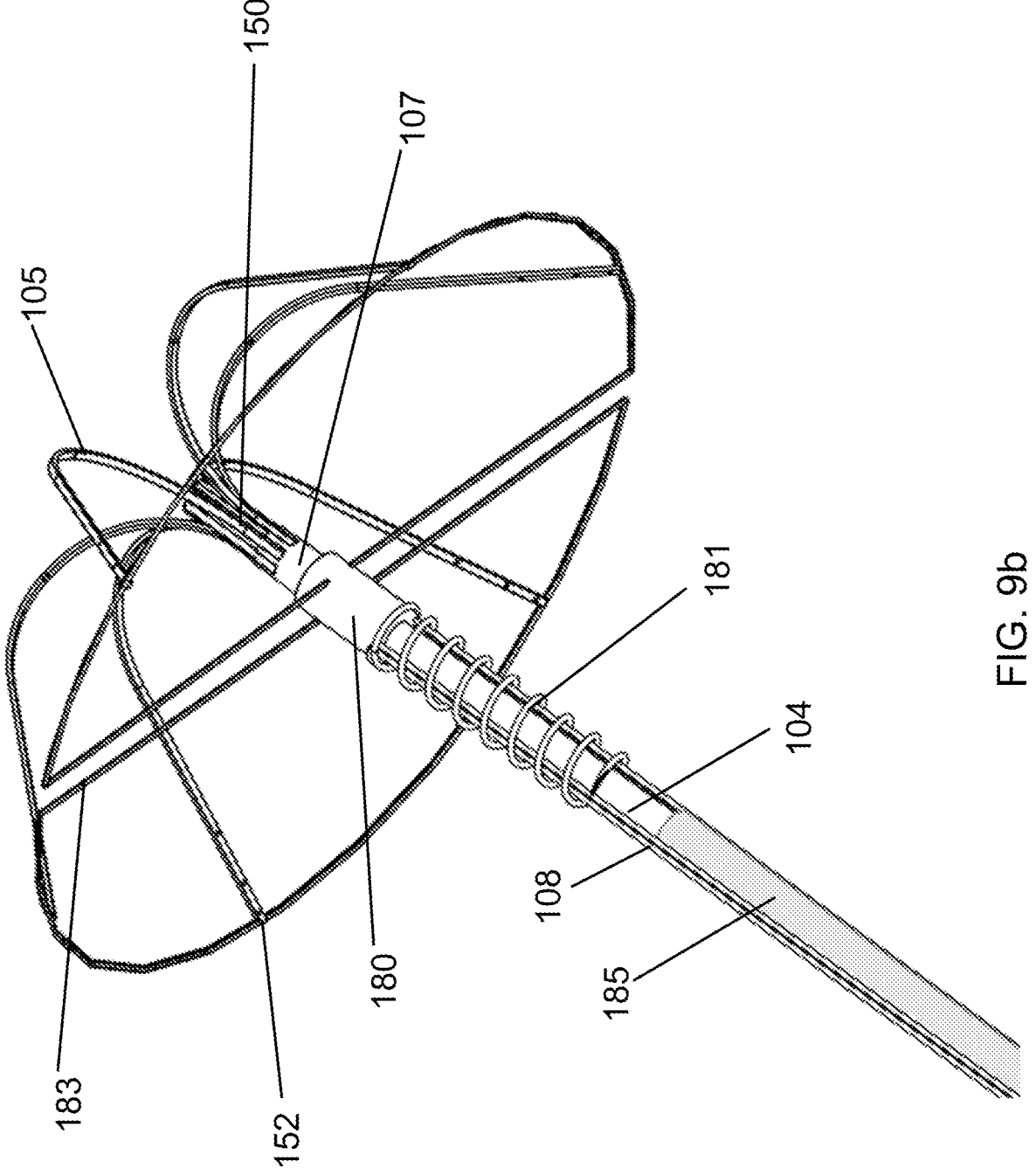
FIG. 9b is another perspective view of the capturing tool of FIG. 9a, wherein a spring and a plurality of drivers are connected to the proximal end of the spring guide.
Figure 11:
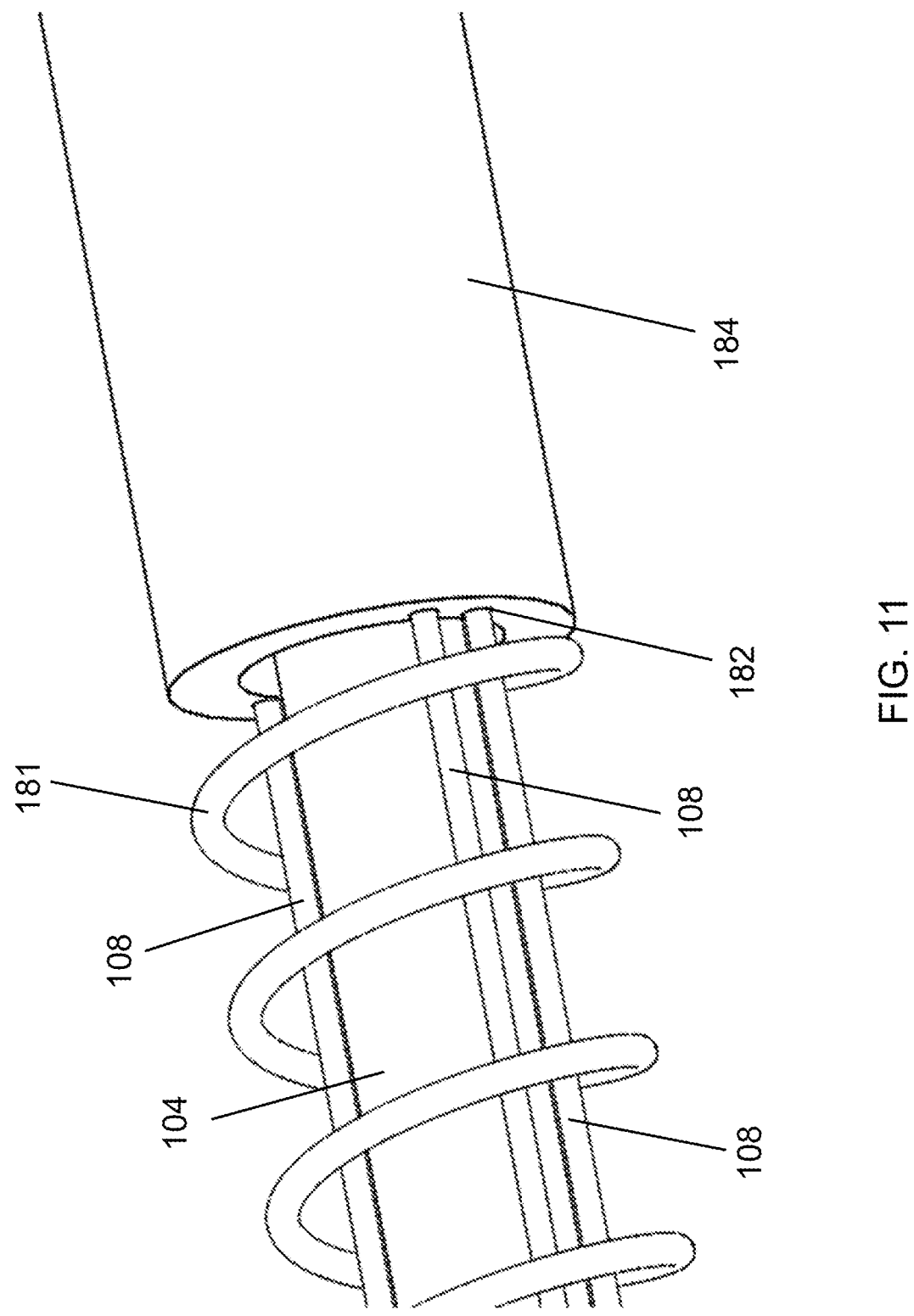

FIGS. 9*a*-9*b* shows the catheter device 100 of FIGS. 3*a*-4 with additional components. For example, the catheter device 100 includes an outer tube 102, a guide tube 184 disposed within the outer tube 102, a support tube 185 disposed within the guide tube 184, and an inner tube 104 disposed within the support tube 185. A spring guide 180 is mounted around the fitting 107 and the distal end of the inner tube 104 and is slidable along the exterior surface of the inner tube 104 in a translation motion. A spring 181 is also provided around the inner tube 104 between the spring guide 180 and a distal end of the guide tube 184. In this particular configuration, the drivers 108 extend through the walls of the guide tube 184 via hollow passages 182 (FIG. 11). The guide tube 184 also connects to the first grip member. The drivers 108 connect to the first grip member and to the proximal end of the spring guide 180, while a set of guide wires 183 can connect the second end 152 of the ribs 105 to the sides of the spring guide 180. The support tube 185 provides support and/or rigidity to prevent any tubes (e.g., guide tube 184, inner tube 104, outer tube 102) from collapsing when the spring 181 is in a loaded position. While the support tube 185 provides rigidity for the spring 181, in some embodiments the support tube 185 can be flexible and still prevent the any tube from unintentional collapsing or flexing. The guide tube 184 and the support tube 185 can both be manufactured from materials including, but not limited to, polymer, plastic, rubber, metal, composite, or any other material known in the art for constructing medical instruments. Further examples of materials that can be used to construct the guide tube 184 and the support tube 185 include, but are not limited to, silicone rubber, polyurethane, polycarbonate, polypropylene, polyethylene, polyester, polystyrene, PVC, polyethersulfone, thermoplastic elastomers, fluoropolymers, Makolon®, Bayfol®, peek, acrylic, stainless steel, titanium, polylactic acid, and any other material known in the art for producing medical instruments and devices.

Referring to FIG. 9*b*, the capturing tool 103 is depicted without the mesh 106, the outer tube 102, and the guide tube 184 for ease in illustrating other elements of the catheter device 100. The guide wires 183 initially extend outward away from the spring guide 180 (in a direction perpendicular to the longitudinal axes of the inner tube and fitting), and then extend in circumferential directions around the longitudinal axis of the inner tube 104, thereby forming two loops (FIG. 10. In some embodiments, the guide wires 183 and the drivers 108 may be the same, wherein the spring guide 180 has two curved passages to redirect the drivers 108 to the second end of the ribs 105. In other embodiments, the guide wires 183 and the drivers 108 may different, wherein the drivers 108 are attached to the proximal end of the spring guide 180 and the guide wires 183 are attached to opposing sides of the spring guide 180.

Figure 9C:
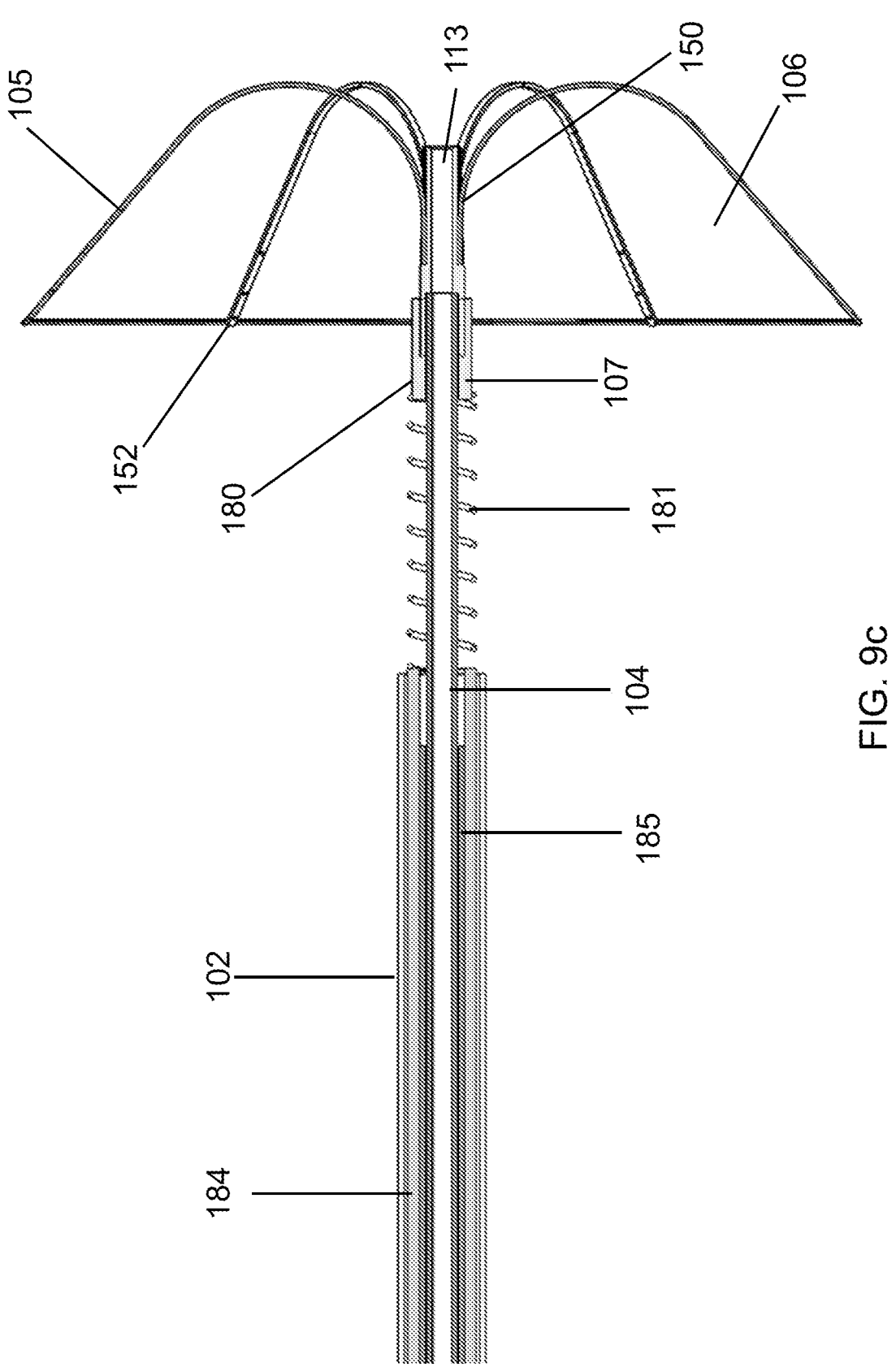
FIG. 9c is a cross-sectional view of the capturing tool of FIG. 9a, wherein the outer tube, guide tube, support tube, and inner tube are shown.

Referring to FIG. 9*c*, the spring guide 180 fits around the inner tube 104 and accepts the proximal end of the capturing tool's fitting 107. The spring 181 is arranged to extend between the distal end of the guide tube 184 and the proximal end of the spring guide 180. In some embodiments, the spring 181 may be in a partially compressed/loaded position before the first grip member 111 is retracted (in a proximal direction), whereas in other embodiments, the spring 181 may be in a fully decompressed/unloaded position before the first grip member 111 is retracted. When the first grip member 111 is pulled in a proximal direction towards a retracted position, the drivers 108 subsequently pull the spring guide 180 along the inner tube 102 in a proximal direction, thereby compelling the spring 181 towards its fully compressed/loaded position. As a result, the guide wires 183 pull on the ribs 105 and/or mesh 106 so that the capturing tool 103 in is a closed/collapsed state. If the user stops exerting force on the first grip member, the first grip member would return to its initial un-retracted position (as a result of the force from the spring 114 within the handle 101) and the spring guide 180 would slide in the distal direction (as a result of the force from spring 181), thereby placing the capturing tool in the open/expanded state.

Figure 10:
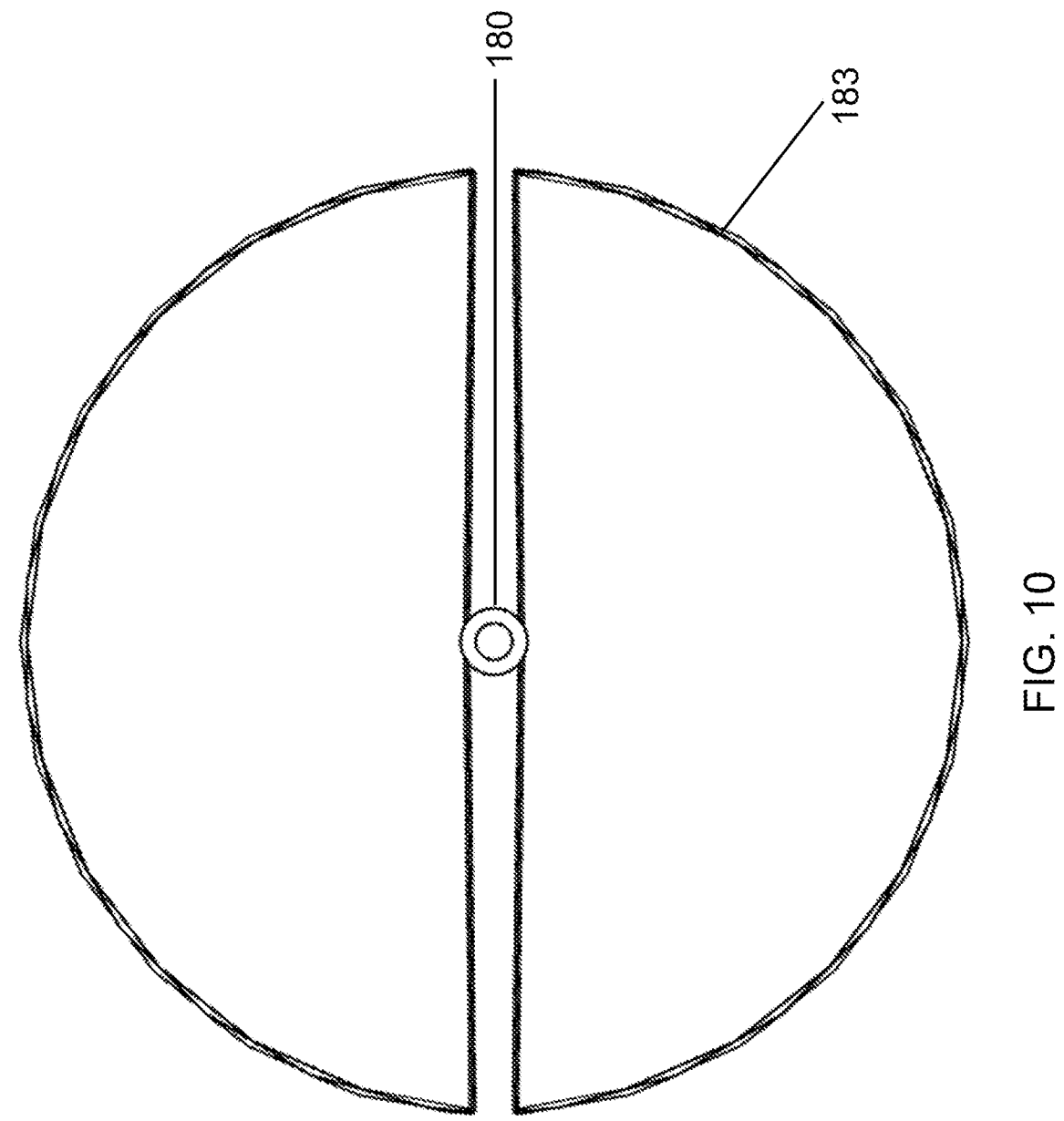

FIG. 10 shows a top view of the guide wires 183 of FIGS. 9*a* and 9*b*. Here, the capturing tool 103 (not pictured) includes two guide wires 183 that connect at the spring guide 180, each forming a half-circle shaped loop. In other embodiments, the capturing tool 103 of the catheter device 101 may only have one guide wire 183 that connects to the spring guide 180, forming a single circular loop. In other embodiments, a plurality of guides wires 183 may be connected to the spring guide and form any number of loops (e.g., two, three, four, five, six, etc.)

Referring to FIG. 11, the spring 181 wraps around the inner tube 104 and the drivers 108. The guide tube 184 comprises two pairs of parallel passages 182 which allow the drivers 108 to extend parallel to the inner tube 104 and the support tube 185. In the starting state of the catheter device 100, the guide tube 184 is covered by the outer tube 102. Where the catheter device 100 includes only one driver 108, then the guide tube 184 has only one hollow passage 182. Where the catheter device 100 includes multiple drivers 1008, then the guide tube 184 includes an appropriate number of hollow passages 182 to accommodate each of the drivers 108 and/or portions of the same driver that are arranged to extending between the handle 101 and the capturing tool 103.

At the beginning of a medical procedure, the entire inner tube 104, guide tube 184, support tube 185, and the capturing tool 103 are typically disposed inside of the bore of the outer tube 102 and shielded from the exterior environment. The capturing tool 103 in particular is in a collapsed or contracted state such that it fits within the outer tube 102. The outer tube 102 is retractable relative to the inner tube 104, the support tube 185, and the guide tube 184 by means of the rotatable fixture 110 so as to expose the capturing tool 103 in its entirety. After retracting the outer tube 102 via the rotatable fixture 110, the capturing tool 103 is exposed or unsheathe from within the outer tube 102 and automatically transitions to the open or expanded position. Once the capturing tool 103 has netted an object present within the body passage, the user pulls the first grip member 111 in a proximal direction to actuate the capturing tool 103. While pulling the first grip member 111 in a proximal direction, the second grip member 112 of the catheter device 100 may pivot relative to the handle 101 for ergonomic support.

The first grip member 111 is used as a slider and shaped such that when the first member 111 is pressed in the proximal direction of the catheter 100, the driver(s) 108 are pulled in a proximal direction which in turn forces the spring guide 180 to move proximally towards the base. As a result, the spring guide 180 compresses the spring 181 into a loaded position and transmits a force to the guide wires 183. This force causes the guide wires 183 to actuate (e.g., pull) the ribs 105 of the capturing tool 103 towards the inner tube 104. When the ribs 105 of the capturing tool 103 are actuated toward the inner tube 104, the capturing tool 103 transitions into a collapsed/closed position. This collapsed/closed position ensures that the netted object is captured and secured inside the capturing tool 103 until the catheter device 100 is fully withdrawn and removed from the body passage.

In some instances, once the capturing tool 103 is in the collapsed/closed position, the outer tube 102 can be advanced or pushed forward (i.e., in a distal direction away from the handle) to re-cover/conceal the capturing tool 103 (by means of the rotatable fixture 110. When the catheter device 100 is removed from the body passage, the user can use the rotatable fixture 110 to re-expose the capturing tool 103. After the capturing tool 103 is exposed outside of the outer tube 102, the capturing tool 103 will automatically return to the open/expanded position (due to the spring 181) once no force is exerted by the user on the first grip member 111, which in turn releases the object from the capturing tool 103.

While the present teachings have been described above in terms of specific embodiments, it is to be understood that they are not limited to those disclosed embodiments. Many modifications and other embodiments will come to mind to those skilled in the art to which this pertains, and which are intended to be and are covered by this disclosure. For example, in some instances, one or more features disclosed in connection with one embodiment can be used alone or in combination with one or more features of one or more other embodiments. It is intended that the scope of the present teachings should be determined by proper interpretation and construction of the appended claims and their legal equivalents, as understood by those of skill in the art relying upon the disclosure in this specification and the attached drawings.

What is claimed is:

1. A catheter device, comprising:
an inner tube having a proximal end and a distal end;
an outer tube disposed around the inner tube;
a capturing tool connected to the distal end of the inner tube, the capturing tool including a mesh adapted to capture an object within a body passage, the outer tube being configured to cover at least a portion of the capturing tool;
a handle connected to a proximal section of the inner tube and configured to retract the outer tube in a proximal direction relative to the inner tube to expose the capturing tool, the handle including:
a base that houses the proximal end of the inner tube and a proximal end of the outer tube;
a rotatable fixture mounted at a distal end of the base and configured to retract the outer tube in the proximal direction in response to rotation in a first direction and to advance the outer tube in a distal direction in response to rotation in a second direction opposite to the first direction,
a first grip member disposed at or proximate to the distal end of the base, the first grip member comprising finger loops on each side of the base;
a second grip member disposed at a proximal end of the base, the second grip member including a finger loop;
wherein at least one of the first grip member or the second grip member is configured to acuate the capturing tool from the expanded position towards the collapsed position; and
a driver connecting the capturing tool to the handle and configured to transmit a force from the handle to the capturing tool to actuate the capturing tool from an expanded position towards a collapsed position, the driver being disposed between the inner tube and the outer tube;
wherein the capturing tool is biased towards the expanded position such that the capturing tool automatically transitions into the expanded position in response the outer tube being retracted in the proximal direction.

2. The catheter device of claim 1, wherein:
the first grip member is configured to slide relative to the base in a proximal direction from a start position to an end position to transmit said force from the first grip member to the capturing tool via the driver to transition the capturing tool from the expanded position to the collapsed position; and
the second grip member is pivotable around a longitudinal axis of the proximal end of the base.

3. The catheter device of claim 2, wherein the handle further comprises:
a spring positioned within the base between the first grip member and a buttress, the spring being wrapped around the proximal section of the inner tube;
wherein the spring is configured to compel the first grip member towards the start position such that the spring becomes loaded or more loaded when the first grip member is forced towards the end position.

4. The catheter device of claim 1, wherein the capturing tool comprises:
a fitting fixed to the distal end of the inner tube; and
a plurality of ribs mounted around the fitting, each rib having a first end connected to the fitting and a second end connected to the driver;
wherein the mesh connects to at least the second end of each rib and is configured to cover a top-side of each rib.

5. The catheter device of claim 4, wherein each rib is configured to extend radially outward away from the inner tube and spread open the mesh when the capturing tool is in the expanded position.

6. The catheter device of claim 4, wherein the fitting is detachable from the distal end of the inner tube.

7. The catheter device of claim 4, wherein at least one rib of the plurality of ribs forms an arc shape from the respective first end and the respective second end.

8. The catheter device of claim 4, wherein the ribs are flexible.

9. The catheter device of claim 1, wherein the catheter device comprises multiple drivers that are positioned between the inner tube and the outer tube and extend from the handle to the capturing tool, each driver being configured to transmit said force from the handle to the capturing tool to actuate the capturing tool from the expanded position towards the collapsed position.

10. The catheter device of claim 1, wherein the driver comprises a suture.

11. The catheter device of claim 1, wherein the mesh comprises a plurality of filaments that are woven together.

12. The catheter device of claim 1, wherein the second grip member is configured to pivot around an axis of the proximal end of the handle base for ergonomic support during operation.

13. A catheter device, comprising:
an inner tube having a proximal end and a distal end;
an outer tube disposed around the inner tube;
a capturing tool connected to the distal end of the inner tube, the outer tube being configured to cover at least a portion of the capturing tool, the capturing tool including:
a fitting that is fixed to the distal end of the inner tube,
a plurality of ribs mounted around the fitting, each rib having a first end connected to the fitting and a second end connected to the driver, and
a mesh that is connected to at least the second end of each rib and configured to cover a top-side of each rib, the mesh being adapted to capture an object within a body passage,
a handle connected to a proximal section of the inner tube and configured to retract the outer tube in a proximal direction relative to the inner tube to expose the capturing tool, the handle including:
a base that houses the proximal end of the inner tube and a proximal end of the outer tube;
a rotatable fixture mounted at a distal end of the base and configured to retract the outer tube in the proximal direction in response to rotation in a first direction and to advance the outer tube in a distal direction in response to rotation in a second direction opposite to the first direction,
a first grip member disposed at or proximate to the distal end of the base; the first grip member comprising finger loops on each side of the base;

a second grip member disposed at a proximal end of the
base, the second grip member including a finger
loop;
wherein at least one of the first grip member or the
second grip member is configured to acuate the
capturing tool from the expanded position towards
the collapsed position; and
a driver connecting the capturing tool to the handle and
configured to transmit a force from the handle to the
capturing tool to actuate the capturing tool from an
expanded position towards a collapsed position, the
driver being disposed between the inner tube and the
outer tube;
wherein the capturing tool is biased towards the expanded
position such that the capturing tool automatically
transitions into the expanded position in response the
outer tube being retracted in the proximal direction;
wherein the handle has a tube port connected to the inner
tube and the fitting has a distal end with an access port
that is connected to the inner tube, such that the tube
port, inner tube and access port form a continuous
channel.
14. The catheter device of claim 13, wherein the fitting is
detachably connected to the distal end of the inner tube to
allow replacement of the capturing tool.

20

* * * * *